United States Patent
Korenaga et al.

(10) Patent No.: US 9,509,893 B2
(45) Date of Patent: Nov. 29, 2016

(54) IMAGING DEVICE AND ANALYZING APPARATUS USING THE IMAGING DEVICE

(71) Applicant: Panasonic Intellectual Property Management Co., Ltd., Osaka (JP)

(72) Inventors: Tsuguhiro Korenaga, Osaka (JP);
Norihiro Imamura, Osaka (JP);
Keiichi Matsuzaki, Kyoto (JP);
Kazuhiro Ochi, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 12 days.

(21) Appl. No.: 14/663,341

(22) Filed: Mar. 19, 2015

(65) Prior Publication Data
US 2015/0281535 A1    Oct. 1, 2015

(30) Foreign Application Priority Data

Mar. 31, 2014  (JP) .................. 2014-074243

(51) Int. Cl.
*H04N 5/225* (2006.01)
*G02B 5/20* (2006.01)
*G02B 5/10* (2006.01)
*G02B 7/00* (2006.01)
*G02B 3/00* (2006.01)
*G02B 13/00* (2006.01)
(Continued)

(52) U.S. Cl.
CPC .......... *H04N 5/2254* (2013.01); *G01N 21/314* (2013.01); *G01N 21/359* (2013.01); *G01N 33/025* (2013.01); *G02B 3/0006* (2013.01); *G02B 5/10* (2013.01); *G02B 5/201* (2013.01); *G02B 7/006* (2013.01); *G02B 13/0015* (2013.01); *G01N 2201/129* (2013.01); *H04N 5/238* (2013.01)

(58) Field of Classification Search
CPC .. H04N 5/2254; H04N 5/238; G01N 21/314; G01N 33/025; G01N 21/359; G01N 2201/129; G02B 7/006; G02B 5/201; G02B 5/10; G02B 3/0006; G02B 13/0015
See application file for complete search history.

(56) References Cited

U.S. PATENT DOCUMENTS 6,326,998 B1 * 12/2001 Palum ................ G02B 27/0988
                                                      348/340
7,433,042 B1    10/2008  Cavanaugh et al.
(Continued)

FOREIGN PATENT DOCUMENTS

JP    2002-287032    10/2002
JP    2011-075562    4/2011
(Continued)

Primary Examiner — Twyler Haskins
Assistant Examiner — Padma Haliyur
(74) Attorney, Agent, or Firm — McDermott Will & Emery LLP

(57) ABSTRACT

An imaging device includes: an optical system having a lens and a diaphragm; an image sensor having a first pixel and a second pixel which a light that has passed through the optical system enters; and an optical element array positioned between the optical system and the image sensor, the optical system has an optical filter including a first region and a second region having different optical characteristics, the optical element array makes the light that has passed through the first region enter the first pixel and makes the light that has passed through the second region enter the second pixel, and an entrance pupil of the optical system is located between the diaphragm and an object.

22 Claims, 17 Drawing Sheets

(51) Int. Cl.
*G01N 21/359* (2014.01)
*G01N 33/02* (2006.01)
*G01N 21/31* (2006.01)
*H04N 5/238* (2006.01)

(56) References Cited

U.S. PATENT DOCUMENTS

2010/0241357 A1\* 9/2010 Chan .................. G01J 3/44
                                                      702/19
2011/0073752 A1    3/2011  Berkner et al.
2012/0182438 A1    7/2012  Berkner et al.
2012/0268643 A1\* 10/2012  Imamura ............... H04N 5/332
                                                      348/335
2014/0055661 A1    2/2014  Imamura et al.

FOREIGN PATENT DOCUMENTS

| JP | 2012-150112 | 8/2012 |
| JP | 2013-258647 | 12/2013 |
| WO | 2013/114891 | 8/2013 |
| WO | 2013/179620 | 12/2013 |
| WO | 2014/045596 | 3/2014 |

\* cited by examiner

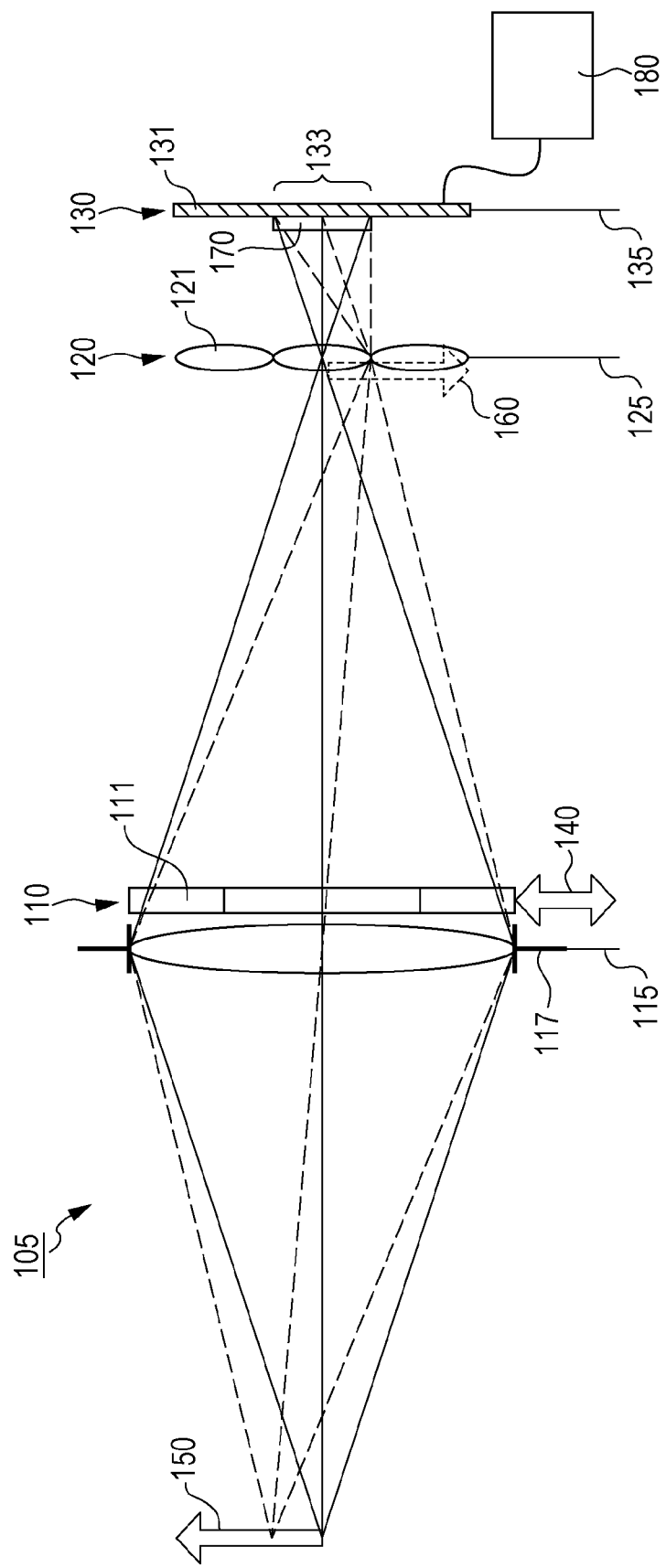

IMAGING DEVICE AND ANALYZING APPARATUS USING THE IMAGING DEVICE

BACKGROUND

1. Technical Field

The present disclosure relates to an imaging device such as a camera and an analyzing apparatus using the imaging device.

2. Description of the Related Art

There is a growing need for an imaging device that not only acquires a color image, but also has other functions. In particular, recently, there has been an increase in research and development in the field of spectroscopic imaging that performs image acquisition for each of a plurality of wavelengths.

In spectroscopic imaging, by acquiring two-dimensional brightness information of an object for a plurality of wavelengths or wavelength bands, it is possible to sense useful information that is difficult or impossible to sense only by visual inspection of the object. These information includes, for example, the degree of freshness or the sugar content of vegetables or fruits, extraction of a foreign body in various product inspection lines, and identification of diseased tissue by analysis of fluorescence that is generated as a result of an object being irradiated with excitation light.

There are mainly two methods for performing spectroscopic imaging, One is a method by which a plurality of illumination light sources, each having a specific wavelength, are prepared and an object is illuminated thereby with switching being performed between the illumination light sources and, at the same time, images of the object are taken by an imaging device at emission of each illumination light source. The other is a method by which an object is illuminated by a light source, such as a white light source, which has a wide wavelength band and an image thereof is acquired by an imaging device via a spectral filter that allows only a desired wavelength to pass therethrough.

A suitable method of the above-described two methods is selected depending on an object to be measured or an environment and circumstances in which measurement is performed. The latter has the advantage that the flexibility for the number of wavelengths or the wavelength bandwidth that can be acquired is high and spectroscopic imaging can be performed relatively easily. As a specific example, a filter wheel provided with a plurality of spectral filters having different transmission wavelength bands is positioned in front of an imaging device and switching between the spectral filters is performed, whereby a plurality of images having different wavelength bands can be sequentially acquired.

U.S. Pat. No. 7,433,042 and Japanese Unexamined Parent Application Publication No. 2011-75562 disclose examples in which a plurality of wavelength images are acquired at the same time by one imaging device.

SUMMARY

In general, a wavelength that is allowed by a spectral filter to pass therethrough varies with the angle of incidence of a light beam entering the spectral filter. This makes it difficult to perform spectroscopic imaging at a wide angle of view in a desired narrow wavelength band.

One non-limiting and exemplary embodiment provides an imaging device and an analyzing apparatus that can perform spectroscopic imaging in a narrow wavelength band at a wide angle of view.

In one general aspect, the techniques disclosed here feature an imaging device including an optical system having a lens and a diaphragm, an image sensor having a first pixel and a second pixel which a light that has passed through the optical system enters, and an optical element array positioned between the optical system and the image sensor, in which the optical system has an optical filter including a first region and a second region having different optical characteristics, the optical element array makes a light that has passed through the first region enter the first pixel and makes a light that has passed through the second region enter the second pixel, and an entrance pupil of the optical system is located between the diaphragm and an object.

With the imaging device in the present disclosure, it is possible to perform spectroscopic imaging in a narrow wavelength band at a wide angle of view.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 21 is a configuration diagram of a multimode light irradiation field image-forming system disclosed in Japanese Unexamined Patent Application Publication No. 2011-75562 as an existing example.

DETAILED DESCRIPTION (Underlying Knowledge Forming Basis of the Present Disclosure)

The inventor has found out that the following problems arise in a wavelength band and an angle of view in spectroscopic imaging described in the "Description of the Related Art" section.

As described in the "Description of the Related Art" section, U.S. Pat. No. 7,433,042 and Japanese Unexamined Patent Application Publication No. 2011-75562 disclose the techniques of acquiring a plurality of wavelength images at the same time by one imaging device.

Figure 20A:
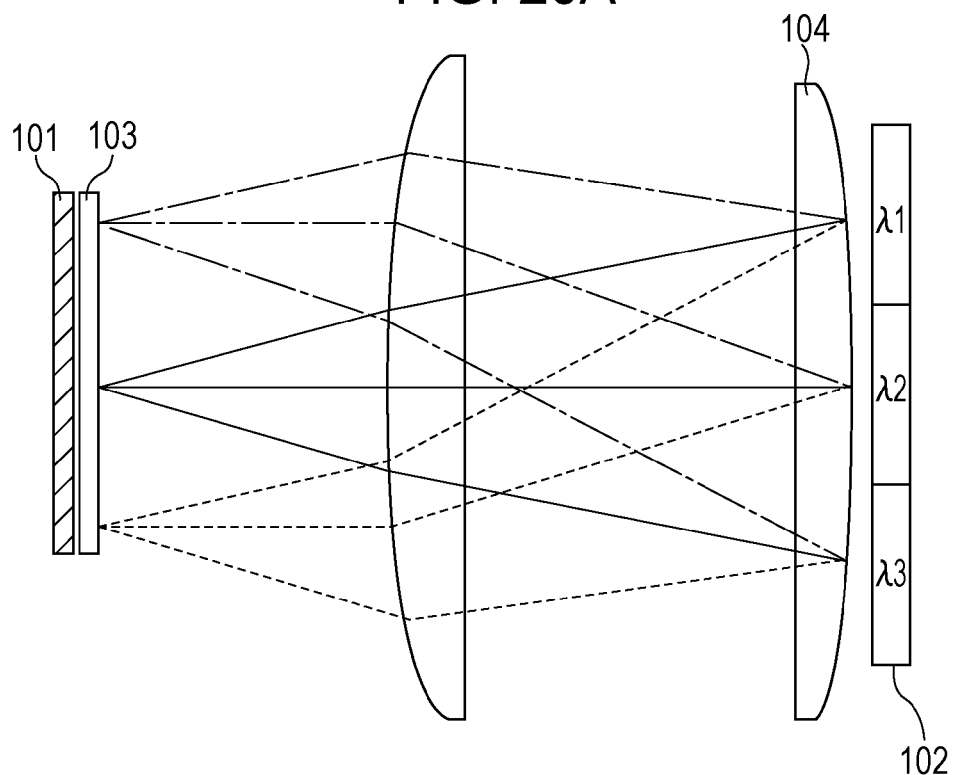
FIG. 20A is a diagram depicting an example of an imaging device disclosed in U.S. Pat. No. 7,433,042 as an existing example.
Figure 20B:
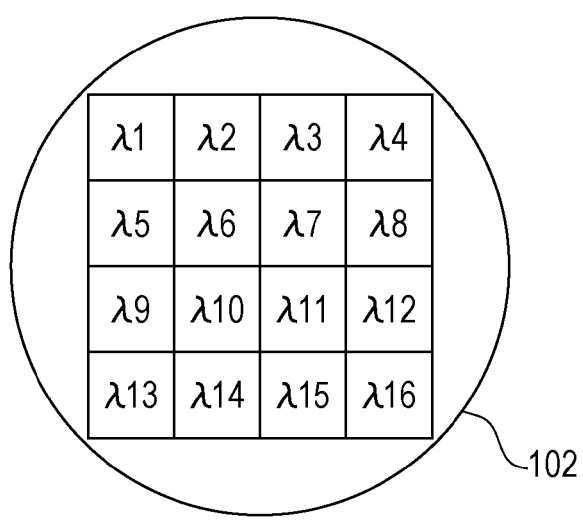
FIG. 20B is a diagram depicting a color filter array disclosed in U.S. Pat. No. 7,433,042.

FIG. 20A is a diagram depicting an example of an imaging device disclosed in U.S. Pat. No. 7,433,042. FIG. 20B is a diagram depicting a color filter array 102 of this imaging device. The color filter array 102 formed of 16 (=4×4) types of color filters as in FIG. 20B is located in the position of the entrance pupil of a lens 104. Immediately below a microlens array 103, an image sensor 101 is present, 4×4 pixels are disposed below each individual microlens, and light beams that have passed through different color filters are taken in by the pixels. The imaging device that acquires the images having 16 types of wavelength information at the same time in this manner is disclosed.

FIG. 21 is a configuration diagram of a multimode light irradiation field image-forming system disclosed in Japanese Unexamined Patent Application Publication No. 2011-75562. An optical image 160 of an object 150 is formed on an image plane surface 125 by an optical module 105. The light that has passed through a filter array 118 is separated by a microlens array 120, and the light beams that have passed through the filters of the filter array 110 form images separately in a detector array 130. The system that can acquire the images having the transmission wavelength information of the filters provided in the filter array 118 at the same time in this manner and can change the filters to filters having different spectral characteristics by moving the filter array 110 with an actuator 140 is described.

In general, the wavelength that is allowed by a spectral filter to pass therethrough varies with the angle of incidence of a light beam entering the spectral filter. This makes it difficult to perform spectroscopic imaging in a narrow wavelength band at a wide angle of view.

As the spectral filter, a calor filter using a material having wavelength dependence as absorption characteristics and an interference filter formed of an optical multilayer film formed as stacked films made of materials with different refractive indexes are representative examples. In particular, with the interference filter formed of an optical multilayer film, it is possible to implement a narrow-band-pass filter that allows only a specific wavelength to pass therethrough. Furthermore, this filter can implement various filter characteristics such as a band-pass filter, a high-pass filter, and a low-pass filter, and the light use efficiency thereof is higher than that of an absorption-type spectral filter and the degree of flexibility in setting spectral transmission characteristics is also high. On the other hand, the wavelength separated by transmission or reflection with respect to the angle of incidence of a light beam markedly shifts. In the imaging device, light beams emitted from an object are collected and, since the greater the angle of view of the imaging device becomes, the more likely the light beams are to enter the optical system obliquely, it is impossible to obtain desired spectral characteristics. In particular, in a layout in which the interference filter is positioned in front of the imaging device, the problem of the layout making it impossible to take images at a wide angle of view has become pronounced.

In the imaging device disclosed in U.S. Pat. No. 7,433,042, an example in which a spectral filter is provided in the imaging device is disclosed. However, since a spectral filter array is disposed in the position of an entrance pupil, a light beam that enters the spectral filter has an angular width, and the problem of this making it difficult to acquire light beam information on a specific narrow wavelength width and an image arises. Moreover, also in Japanese Unexamined Patent Application Publication No. 2011-75562, no consideration is given to the angle of incidence of a light beam entering the spectral filter, and therefore the same problem arises especially when an image of an object is taken at a wide angle of view.

To solve these problems, an imaging device according to an aspect of the present disclosure includes: an optical system having a lens and a diaphragm; an image sensor having a first pixel and a second pixel which the light that has passed through the optical system enters; and an optical element array positioned between the optical system and the image sensor, the optical system has an optical filter including a first region and a second region having different optical characteristics, the optical element array makes the light that has passed through the first region enter the first pixel and makes the light that has passed through the second region enter the second pixel, and an entrance pupil of the optical system is located between the diaphragm and an object.

With this configuration, it is possible to perform spectroscopic imaging in a narrow wavelength band at a wide angle of view. More specifically, it is possible to implement an imaging device that maintains a spectral wavelength at a high degree of accuracy even at the time of acquisition of a wide-angle image. The wide angle makes it possible to increase an object target area and reduce the number of imaging devices. Moreover, since it is possible to take an image of a target object at close range, it is possible to reduce the sizes of a system and analyzing equipment which are equipped with the imaging device.

Hereinafter, embodiments of the imaging device according to the present disclosure will be described with reference to the drawings.

Incidentally, all the embodiments which will be described below are comprehensive or specific examples. The numerical values, shapes, materials, component elements, placement positions and connection configurations of the component elements, steps, order of steps, and so forth which will be described in the following embodiments are mere examples and are not meant to limit the claims. Moreover, of the component elements in the following embodiments, a component element which is not described in an independent claim describing the broadest concept is described as an arbitrary component element.

(Embodiment 1)

Figure 1:
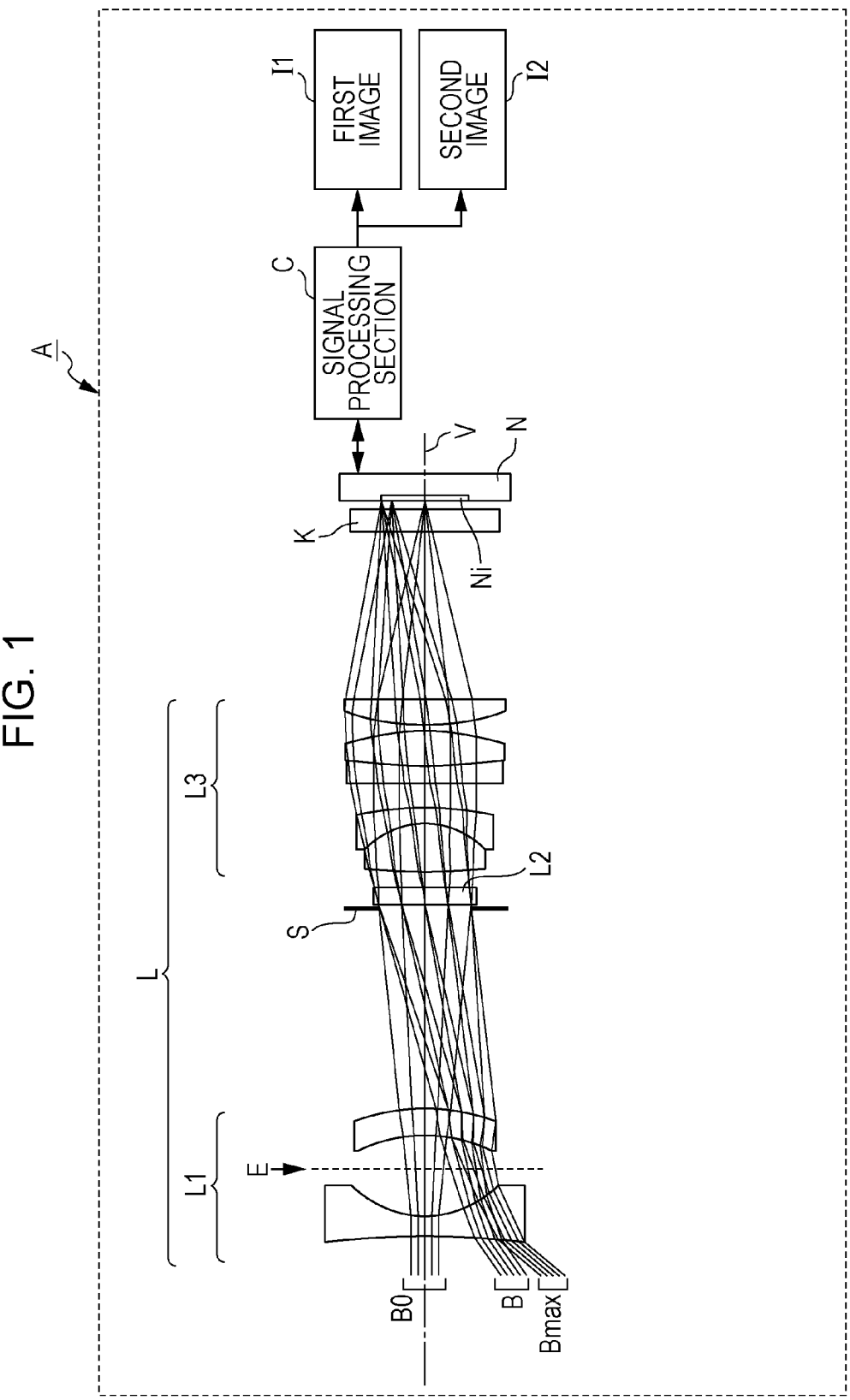
FIG. 1 is a schematic diagram depicting the configuration of an imaging device in Embodiment 1.

FIG. 1 is a schematic diagram depicting an imaging device A of Embodiment 1. The imaging device A of this embodiment includes a lens optical system L having an optical axis V, an optical element array K positioned near the focus of the lens optical system L, an image sensor N, and a signal processing section C.

The lens optical system L is formed of a first element optical system Li having at least one lens, a diaphragm S, an optical filter L2, and a second element optical system L3. The light beam direction of the light that has entered the imaging device A from an object (not depicted in the drawing) is bent by the first element optical system L1, and an unnecessary light beam is removed by the diaphragm S. The optical filter L2 has regions D1 and D2 that allow respectively narrow wavelength bands having different wavelengths λ1 and λ2 as the peaks thereof to pass therethrough and is positioned near the diaphragm S.

This lens optical system L is configured in such a way that an entrance pupil E is located in a position closer to the object than the diaphragm S. Here, the entrance pupil is an image of a diaphragm obtained when a lens is viewed from the side where an object is located, that is, an image of the diaphragm obtained by a lens group that is located from the diaphragm to the side where the subject is located. To be brief, the entrance pupil is an effective aperture of a lens that is determined by a diaphragm. It is for this reason that the entrance pupil is also called an effective aperture. Moreover, the position of an entrance pupil is defined as a position in which a main light beam in an object space intersects with the optical axis after being extended as it is. The object space refers to a space from the object to the entrance to the imaging device A (in FIG. 1, to the entrance to the first element optical system L1). Here, the main light beam refers to a light beam passing through the center of the diaphragm and, in general, refers to a light beam passing through the center of a pencil of rays having an angle of view.

Figure 2:
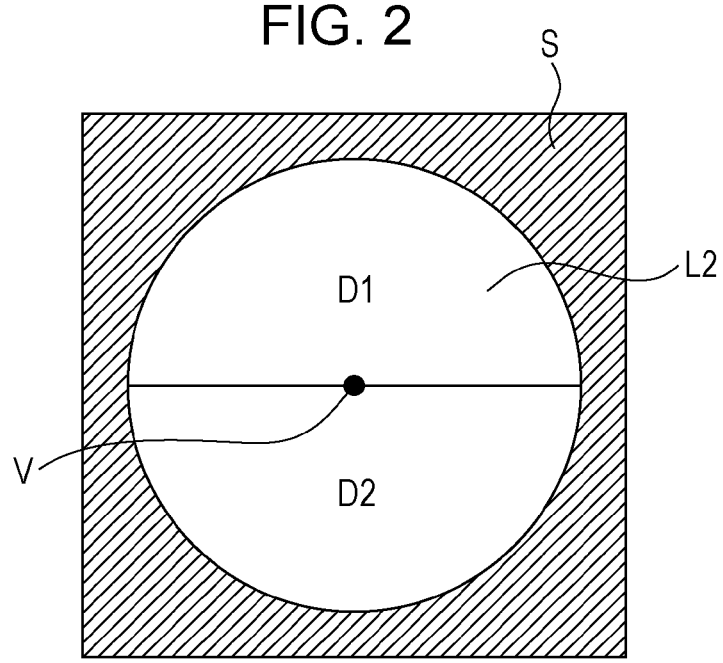
FIG. 2 is a front view of an optical filter provided with optical surface regions that allow different wavelengths to pass therethrough, the optical filter viewed from the side where an object is located, in the imaging device in Embodiment 1.

FIG. 2 is a front view of the optical filter L2 viewed from the side where the object is located, and the regions D1 and D2 are located on an upper side and a lower side, respectively, with the optical axis V located at the center of the boundary between the regions D1 and D2. Moreover, in FIG. 2, the diaphragm S is depicted. The optical filter L2 includes regions having different optical characteristics in a plane which is substantially perpendicular to the optical axis.

Figure 3:
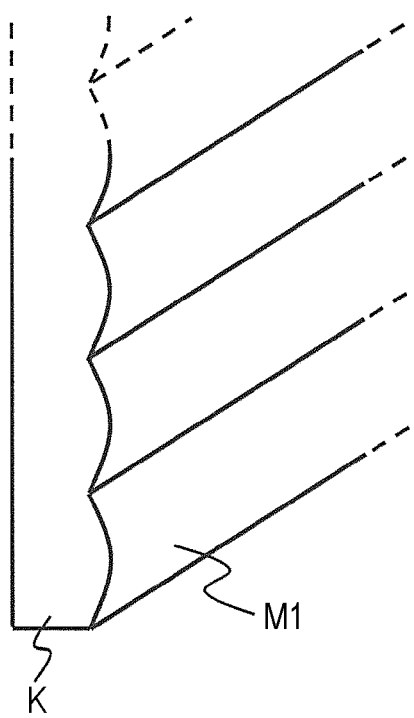
FIG. 3 is a perspective view of an optical element array of the imaging device in Embodiment 1.

FIG. 3 is a perspective view of the optical element array K. Since one optical element M1 of the optical element array K has an arc-shaped section, the optical element array K is a lenticular lens.

Moreover, in FIG. 1, a pencil of rays B0 is a pencil of rays entering the imaging device A from an object located in front of the imaging device A, that is on an extension of the optical axis V, a pencil of rays B is an arbitrary pencil of rays entering the imaging device A from an object located in an oblique direction (an angle which the pencil of rays B forms with the optical axis V is ω), and a pencil of rays Bmax is a pencil of rays entering the imaging device A from an object at the maximum angle of view (an angle which the pencil of rays Bmax forms with the optical axis V is ωmax) of the imaging device A.

The pencil of rays B0 passes through the first element optical system L1 and reaches the diaphragm S and the optical filter L2. In FIG. 1, a pencil of rays of the pencil of rays B0, the pencil of rays above the optical axis V, passes through the region D1. Moreover, a pencil of rays of the pencil of rays B0, the pencil of rays below the optical axis V, passes through the region D2. Then, the pencil of rays B0 passes through the second element optical system L3 and the optical element array K in this order and reaches an imaging surface Ni on the image sensor N. The same goes for the pencils of rays B and Bmax.

Figure 4A:
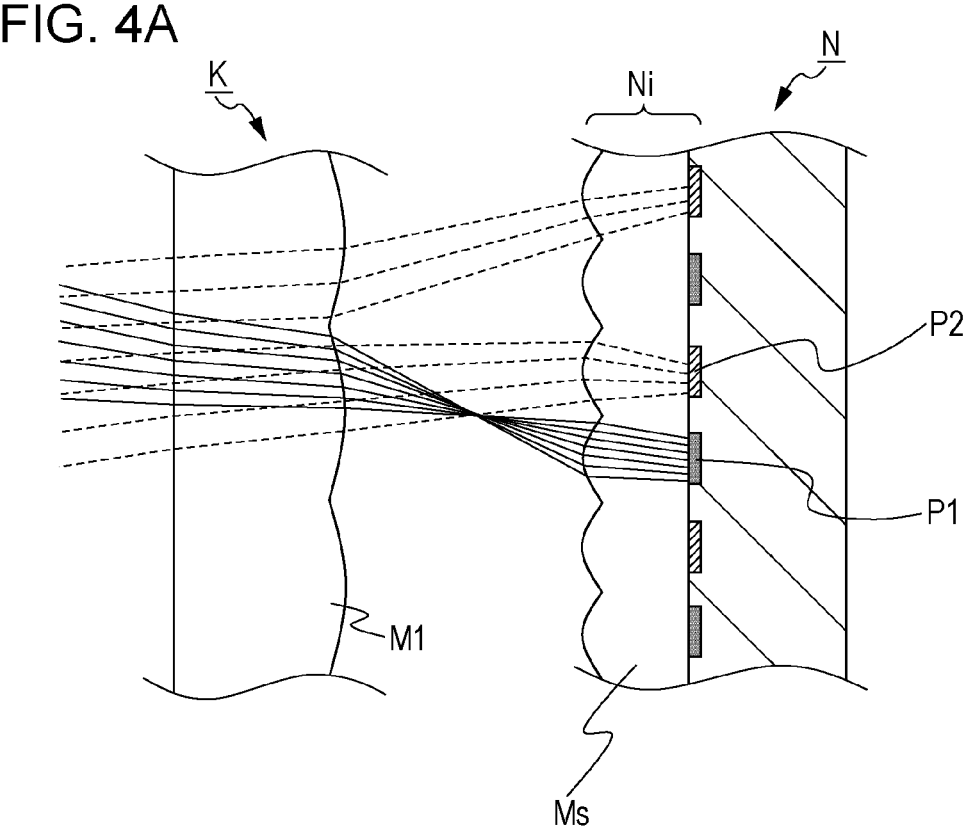
FIG. 4A is an enlarged view of an area near an imaging surface of the imaging device in Embodiment 1.
Figure 4B:
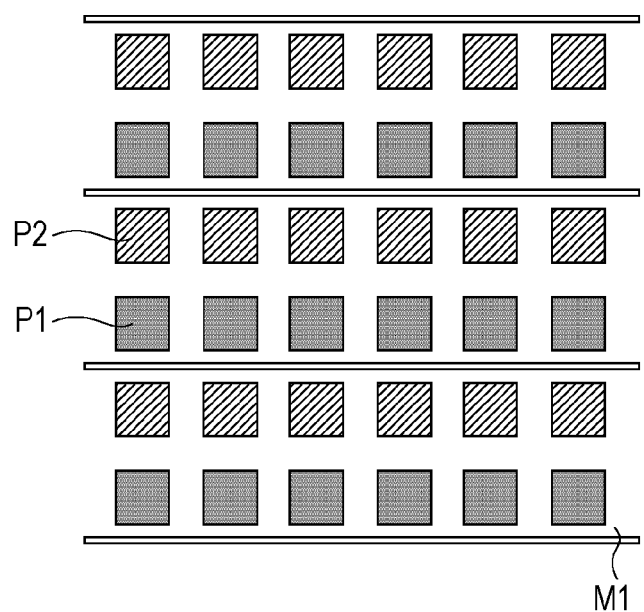
FIG. 4B is a diagram depicting the positional relationship between the optical element array and pixels on an image sensor in Embodiment 1.

FIG. 4A is an enlarged view of the optical element array K and the image sensor N depicted in FIG. 1, and FIG. 4B is a diagram depicting the positional relationship between the optical element array K and pixels on the image sensor N. The optical element array K is positioned near the focus of the lens optical system L and is placed in a position away from the imaging surface Ni at a predetermined distance. Moreover, on pixels P1 and P2 on the imaging surface Ni, microlenses Ms are provided.

Furthermore, the optical elements M1 of the optical element array K are positioned so as to be located on the side where the imaging surface Ni is located and are configured such that one optical element M1 corresponds to two lines of pixels formed of the pixels P1 and the pixels P2 on the imaging surface Ni.

With such a configuration, most of the pencils of rays (solid lines of FIG. 4A) that have passed through the region D1 on the optical filter L2 depicted in FIG. 2 reach the pixels P1 on the imaging surface Ni, and most of the pencils of rays (broken lines of FIG. 4A) that have passed through the region D2 reach the pixels P2 on the imaging surface Ni.

Here, by the signal processing section C depicted in FIG. 1, a first image I1 formed only of the pixels P1 and a second image I2 formed only of the pixels P2 are output.

The first image I1 and the second image I2 are images obtained by the passage through the region D1 and the region D2 of the optical filter L2, respectively; in this way, it is possible to acquire images having different wavelengths λ1 and λ2 at the same time.

Figure 5:
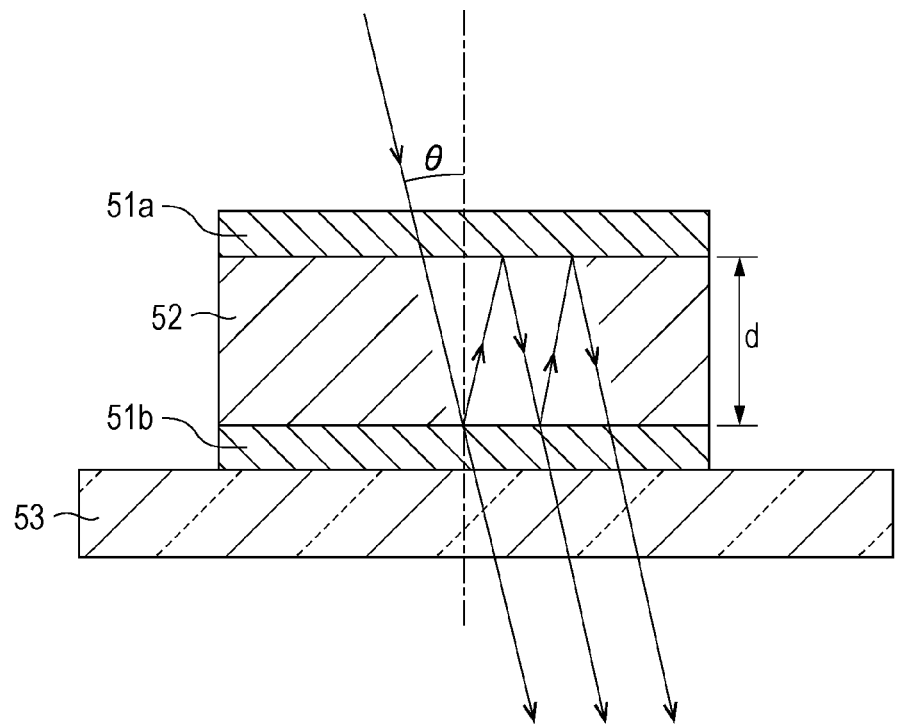
FIG. 5 is a diagram depicting a common Fabry-Perot interference filter.

The optical filter L2 has formed therein a filter with a narrow wavelength band. Hereinafter, as a representative example, a Fabry-Perot interference filter formed of a dielectric multilayer film, the Fabry-Perot interference filter depicted in FIG. 5, will be described. The Fabry-Perot interference filter has a multilayer film structure in which reflection interference surfaces 51a and 51b face each other in a state in which they are parallel to each other on a transparent glass substrate 53 with a spacer layer 52 having a thickness of d and a refractive index of n sandwiched between the reflection interference surfaces 51a and 51b. Though not depicted in the drawing, the reflection interference surfaces 51a and 51b each have a structure in which a high refractive index film and a low refractive index film, each having an optical thickness of λ0/4, are stacked alternately. λ0 is a design wavelength passing through the filter.

When light beams enter such a structure, the light beams are repeatedly reflected by the reflection interference surfaces 51a and 51b and interfere with each other, and only a light with a wavelength that resonates in the spacer layer 52 passes through the filter. If a transmission wavelength is assumed to be λ, the following Expression (1) is obtained.

$$k\lambda = 2nd \cos \theta \quad (1)$$

Here, k is a natural number and θ is an angle formed by a filter normal and an incident light beam.

Figure 6:
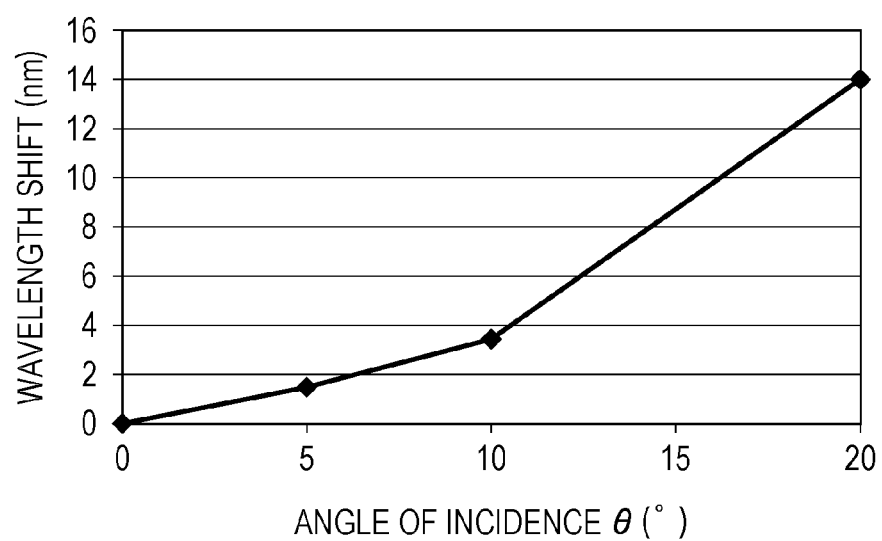
FIG. 6 is a graph of a transmission wavelength shift caused by changes in the angle of incidence to a narrow-band-pass filter.

FIG. 6 is a graph of a transmission wavelength shift caused by changes in the angle of incidence to the narrow-band-pass filter. As is clear from FIG. 6, when a light beam enters the narrow-band-pass filter obliquely, an apparent thickness of the film is reduced by cos θ and the transmission wavelength shifts to the side where the short wavelength is located. In particular, the greater the angle of incidence becomes, the more pronounced a wavelength shift becomes.

Figure 7:
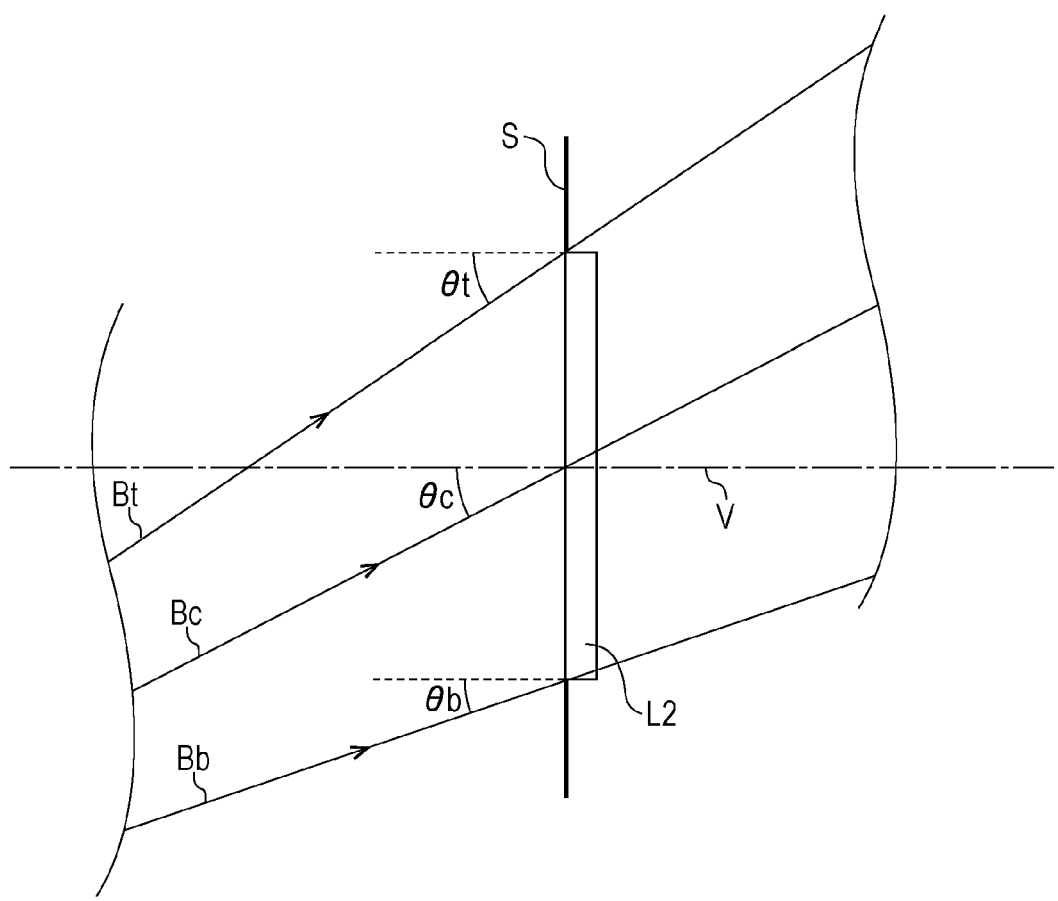
FIG. 7 is an enlarged view of a portion of Embodiment 1, the portion in which a pencil of rays entering the imaging device from the object enters the optical filter.

FIG. 7 is an enlarged view of a portion in which the pencil of rays B entering the imaging device from the object enters the optical filter L2. The angles of light beams entering the optical filter L2 are expressed as θc, θt, and θb for a main light beam Bc passing through the center of the diaphragm, a light beam Bt passing through the upper end of the diaphragm, and a light beam Bb passing through the lower end of the diaphragm, respectively. The angles θc, θt, and θb are different angles and have the relationship θt>θc>θb. As a result, light beams enter the region D1 of the optical filter L2 at an angle between θc and θt and enter the region D2 at an angle between θc and θb. The light beams that have entered the regions D1 and D2 of the optical filter L2 become light beams having different wavelengths after passing through the optical filter L2, but these light beams are mixed as a result of being collected when they reach the pixels P1 and P2. As the aperture shape of the diaphragm S, a circular shape, a rectangular shape, or the like is used; in either case, the proportion of the main light beam passing through the center of the diaphragm is high and the heaviest weight is assigned thereto when the light beam reaches the pixel. It is for this reason that actually no problem arises even when the pencil of rays B is considered to enter the region D1 and the region D2 of the optical filter L2 apparently at an angle corresponding to the angle θc of the main light beam Bc.

in the imaging device of this embodiment, as depicted in FIG. 1, the entrance pupil E is located in a position closer to the object than the diaphragm S and the optical filter L2 near the diaphragm S. At this time, between an angle ω (that is, an angle of view) which the main light beam Bc forms with the optical axis V in the object space and an angle θc which the main light beam Bc entering the optical filter L2 after passing through the center of the diaphragm with the optical axis V, ω>θc holds. That is, a necessary and sufficient condition for ω>θc is that the entrance pupil E is located in a position closer to the object than the diaphragm S. This produces the effect of making the angle of a pencil of rays entering the imaging device from the object closer to the optical axis V, that is, the normal of the optical filter L2. The angle θc becomes smaller as the entrance pupil E gets away from the diaphragm S and closer to the object and it is possible to make the angle ωmax which the pencil of rays Bmax forms with the optical axis V greater, the pencil of rays Bmax entering the imaging device at the greatest angle from the side where the object is located, which makes it possible to implement the imaging device as a wider-angle imaging device.

Incidentally, in the first element optical system L1 it is desirable that at least one lens is an optical system having negative light-collecting power. This makes it easier to make the entrance pupil E get closer to the object than the diaphragm S.

Moreover, the imaging device may be configured such that no second element optical system L3 is provided and an image is taken by the first element optical system L1 and the diaphragm S.

Furthermore, the optical filter L2 does not necessarily have to be a flat surface and may be a curved surface. The regions D1 and D2 may have different shapes. By appropriately providing the regions D1 and D2 with different shapes, it is possible to reduce aberration such as chromatic aberration.

In this embodiment, as depicted in FIG. 2, the optical filter L2 is placed in a position closer to a sensor than the diaphragm S; however, the optical filter L2 may be placed in a position closer to the object than the diaphragm S.

In this embodiment, the optical filter L2 has the regions D1 and D2 that allow respectively narrow wavelength bands having different wavelengths λ1 and λ2 as the peaks thereof to pass therethrough. However, the optical filter L2 is not limited thereto as long as the regions D1 and D2 have different optical characteristics. In particular, the greater the change in the optical characteristics for the angle of incidence of a light beam entering the optical filter L2, the more effective. For example, in a polarizing filter, the amount of transmitted light changes depending on an angle of incidence, and the amount of transmitted light is reduced as the angle of incidence gets greater and a brightness distribution is generated in a camera image. The imaging device in the present disclosure is highly effective also in a case in which such a polarizing filter is used and is effective, in addition to the spectral and polarizing filters, in all types of elements in which the optical characteristics change by the angle of incidence. Moreover, a spectral means is not limited to the Fabry-Perot interference filter.

Furthermore, the region D1 and the region D2 of the optical filter L2 have shapes symmetrical with respect to the optical axis V, but the shapes of the region D1 and the region D2 are not limited thereto. The region D1 and the region D2 of the optical filter L2 may have shapes asymmetrical with respect to the optical axis V and the areas thereof may be different from each other. In this case, image generation is performed in consideration of the correlation with each pixel on the imaging surface.

(Embodiment 2)

Embodiment 2 differs from Embodiment 1 in that an optical filter L2 is divided into four regions and a lenticular lens is replaced with a microlens as the optical element array.

Figure 8:
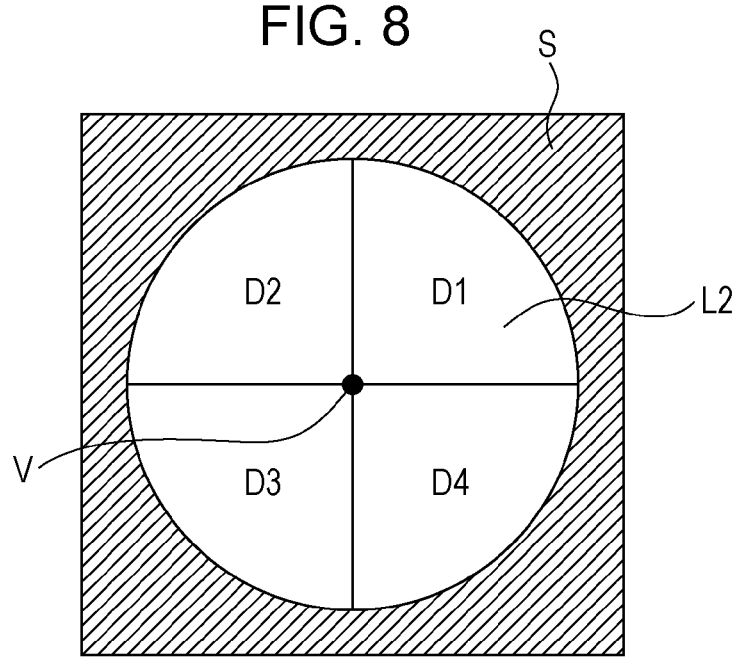
FIG. 8 is a front view of an optical filter provided with optical surface regions that allow different wavelengths to pass therethrough, the optical filter viewed from the side where an object is located, in an imaging device in Embodiment 2.

FIG. 8 is a front view of the optical filter L2 viewed from the side where the object is located. As depicted in FIG. 8, regions D1, D2, D3, and D4 each have the shape of one of portions of the optical filter L2 vertically and horizontally divided into four regions with the optical axis V located at the center of the boundary between the regions D1, D2, D3, and D4. Moreover, the wavelength bands which the regions allow to pass therethrough are different from one another. Furthermore, in FIG. 8, a diaphragm S is depicted.

Figure 9:
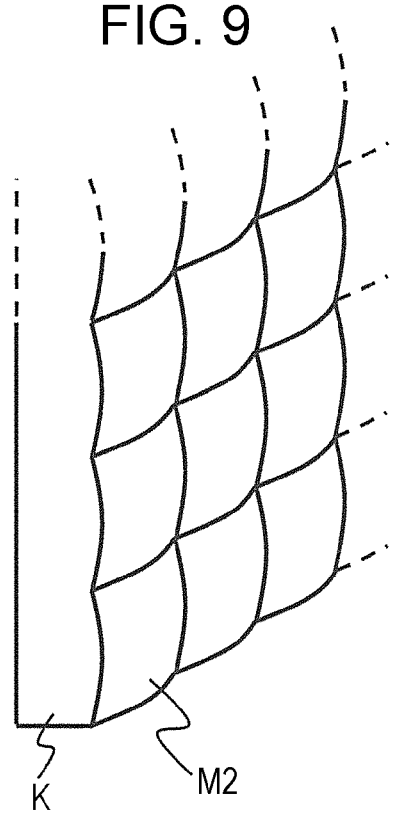
FIG. 9 is a perspective view of an optical element array of the imaging device in Embodiment 2.

FIG. 9 is a perspective view of an optical element array K. One optical element M2 of the optical element array K is a microlens having an arc-shaped section, and the optical element array K is a microlens array.

Figure 10A:
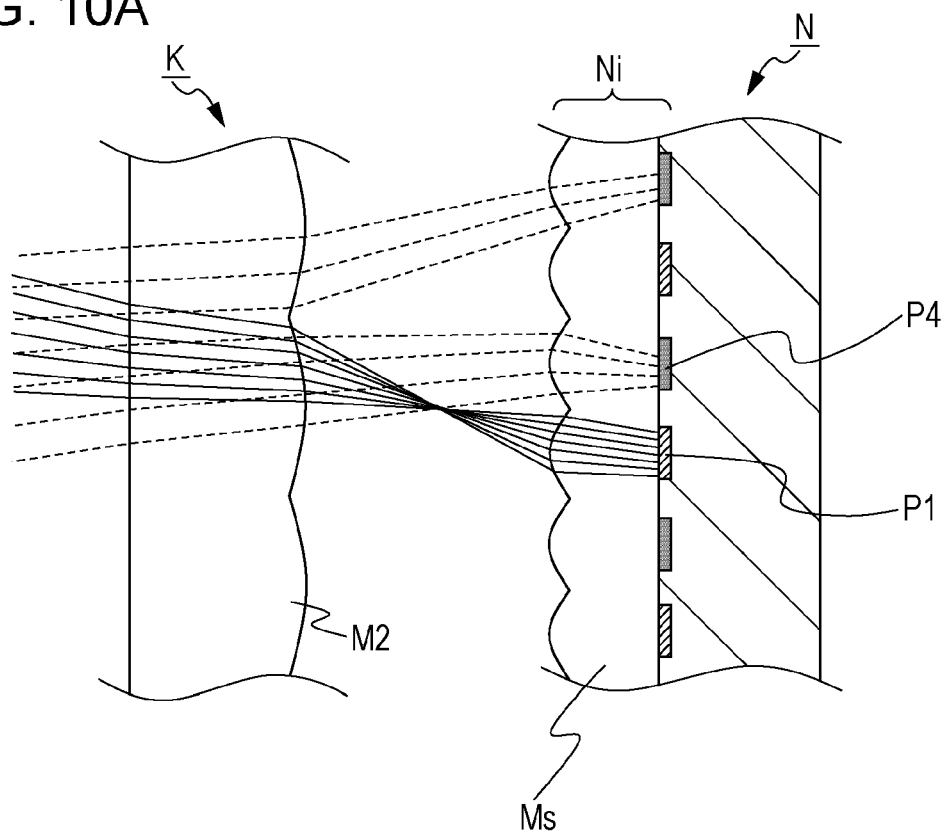
FIG. 10A is an enlarged view of an area near an imaging surface of the imaging device in Embodiment 2.
Figure 10B:
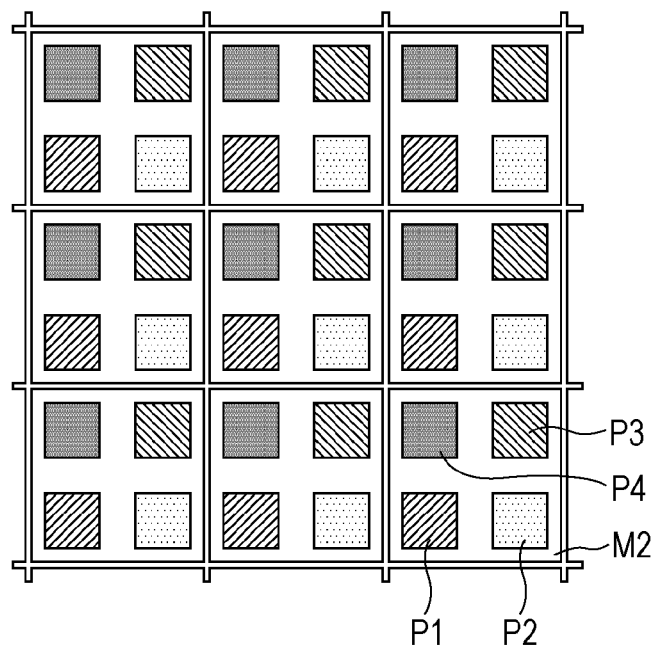
FIG. 10B is a diagram depicting the positional relationship between the optical element array and pixels on an image sensor.

FIG. 10A is an enlarged view of the optical element array K and an image sensor N, and FIG. 10B is a diagram depicting the positional relationship between the optical element array K and pixels on the image sensor N. As is the case with Embodiment 1, the optical element array K is positioned near the focus of a lens optical system L and is placed in a position away from an imaging surface Ni at a predetermined distance. Moreover, on pixels P1 to P4 on the imaging surface Ni, microlenses Ms are provided.

Furthermore, the optical elements M2 of the optical element array K are positioned so as to be located on the side where the imaging surface Ni is located and are configured such that one optical element M2 corresponds to four pixels: the pixels P1 to P4 on the imaging surface Ni.

With such a configuration, most of the pencils of rays that have passed through the region D1 the region D2, the region D3, and the region D4 on the optical filter L2 depicted in FIG. 8 reach the pixel P1, the pixel P2, the pixel P3, and the pixel P4, respectively, on the imaging surface Ni.

Here, as is the case with Embodiment 1, by a signal processing section C, a first image I1, a second image I2, a third image I3, and a fourth image I4 are output.

As a result of providing the region D1, the region D2, the region D3, and the region D4 of the optical filter L2 with different transmission wavelengths, the imaging device A can acquire four images having different wavelength information: the first image I1, the second image I2, the third image I3, and the fourth image I4 at the same time.

Also in this embodiment, as is the case with Embodiment 1, since it is possible to make the angle ωmax which a pencil of rays Bmax entering the imaging device forms with the optical axis V greater, it is possible to implement the imaging device as a wider-angle imaging device without a deviation from a desired wavelength and produce the same effect.

In this embodiment, the optical filter L2 is divided into four different regions; however, the number of divisions may be further increased and the number of pixels corresponding to each optical element M2 may be appropriately changed.

Moreover, the region D1, the region D2, the region D3, and the region D4 of the optical filter L2 have shapes symmetrical with respect to the optical axis V, but the shapes of the region D1, the region D2, the region D3, and the region D4 are not limited thereto. The region D1, the region D2, the region D3, and the region D4 of the optical filter L2 may have shapes asymmetrical with respect to the optical axis V and the areas thereof may be different from each other. The number of pixels corresponding to each optical element may be different from the number of divisions of the optical filter L2.

(Embodiment 3)

Embodiment 3 differs from Embodiments 1 and 2 in that a lenticular lens or a microlens array which is an optical element array is formed in an image sensor.

Figure 11A:
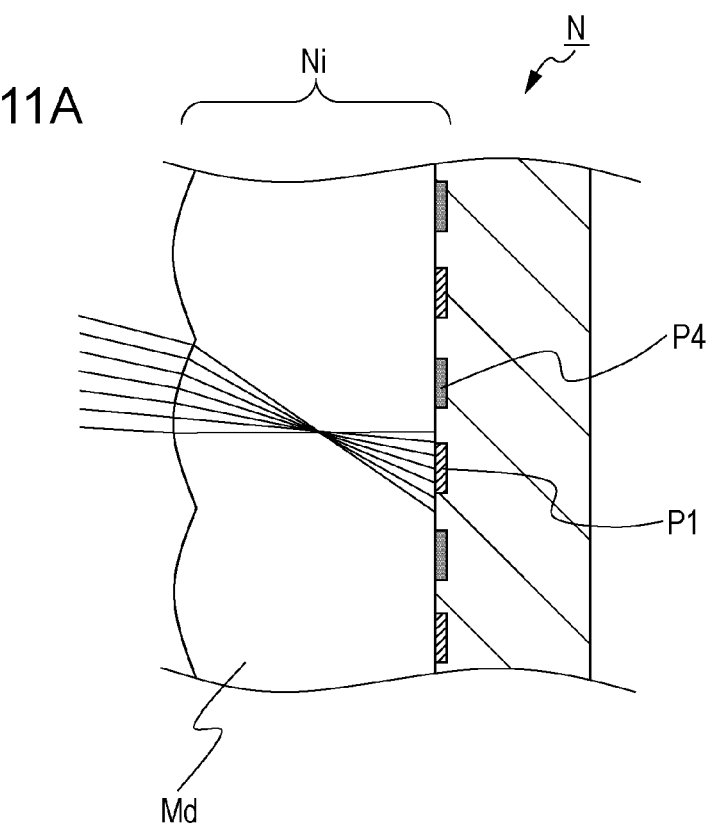
FIG. 11A is a sectional view of an image sensor having an optical element array in Embodiment 3.
Figure 11B:
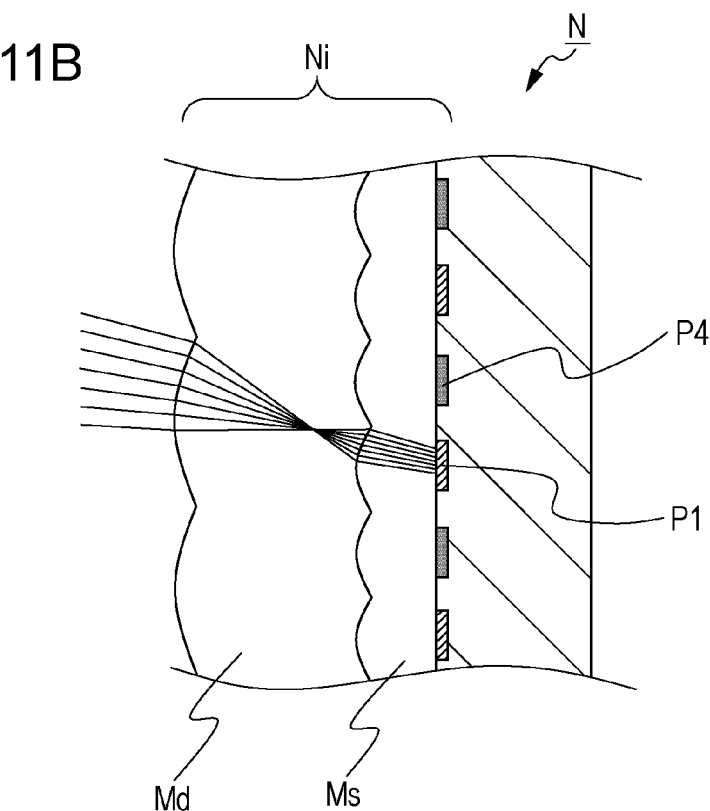
FIG. 11B is a sectional view of an image sensor having microlenses and the optical element array in Embodiment 3.

FIGS. 11A and 11B are sectional views, each depicting an image sensor N having an optical element array Md formed on an imaging surface Ni. The optical element array Md is a lenticular lens or a microlens array, and one optical element of the lenticular lens or one microlens corresponds to a plurality of pixels P1 to P4. Also with such a configuration, as is the case with Embodiments 1 and 2, it is possible to guide the pencils of rays that have passed through different regions on the optical filter L2 to different pixels. Moreover, FIG. 11B depicts a configuration in which the optical element array Md and the microlenses Ms are stacked. With such a configuration, it is possible to achieve higher light-collecting efficiency than the configuration of FIG. 11A.

(Comparative Example)

As a comparative example for the imaging device in the present disclosure, an imaging device of FIG. 12 will be described. An imaging device A of the comparative example includes a lens optical system L having an optical axis V, an optical element array K positioned near the focus of the lens optical system L, an image sensor N, and a signal processing section C.

The lens optical system L is formed of a diaphragm S, an optical filter L2, and a second element optical system L3 having at least one lens. A light that has entered the imaging device A from an object (not depicted in the drawing) enters the optical filter L2 after an unnecessary light beam is removed therefrom by the diaphragm S. The optical filter L2 has regions D1 and D2 that allow respectively narrow wavelength bands having different wavelengths λ1 and λ2 as the peaks thereof to pass therethrough and is positioned near the diaphragm S.

Figure 12:
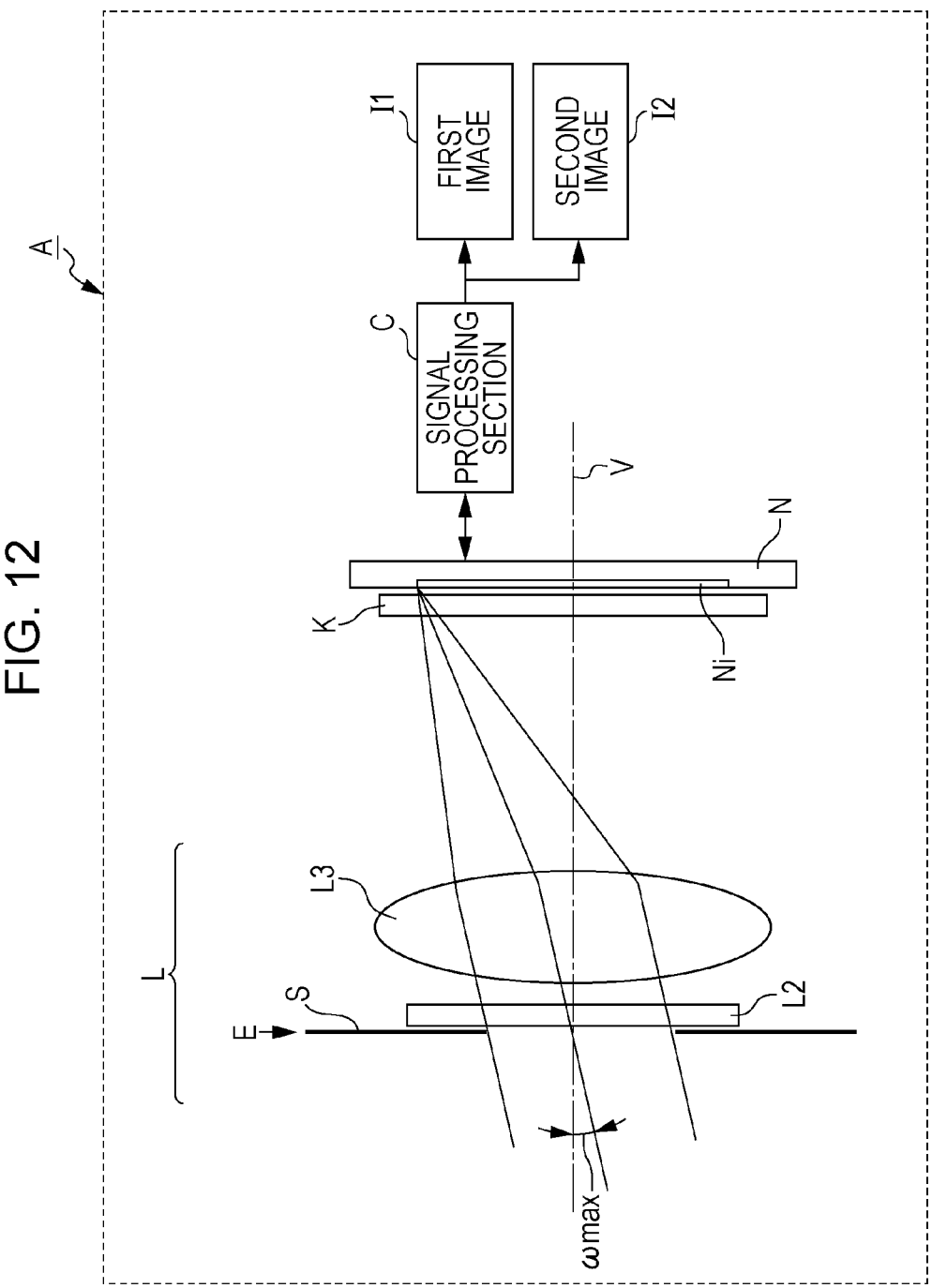
FIG. 12 is a schematic diagram depicting the configuration of an imaging device of a comparative example.

The imaging device of FIG. 12 has a front diaphragm structure in which the diaphragm S is placed in a position closer to the object than the lens optical system L, and the entrance pupil E is placed in the same position as the diaphragm S. As a result of such a placement, a light beam that enters the lens optical system L from the side where the object is located goes straight and enters the optical filter L2 near the diaphragm S without being refracted. Therefore, an angle ωmax which a light beam that enters the imaging device at the maximum angle of view forms with the optical axis V is an angle of incidence at which the light beam enters the optical filter L2. Thus, when the angle of view of the imaging device A is increased, if a spectral filter or a polarizing filter having optical characteristics with heavy angle dependence is provided in the optical filter L2, a spectral wavelength shift and brightness variations on an image occur. That is, it becomes impossible to implement the imaging device as a wider-angle imaging device.

(Embodiment 4)

Figure 13:
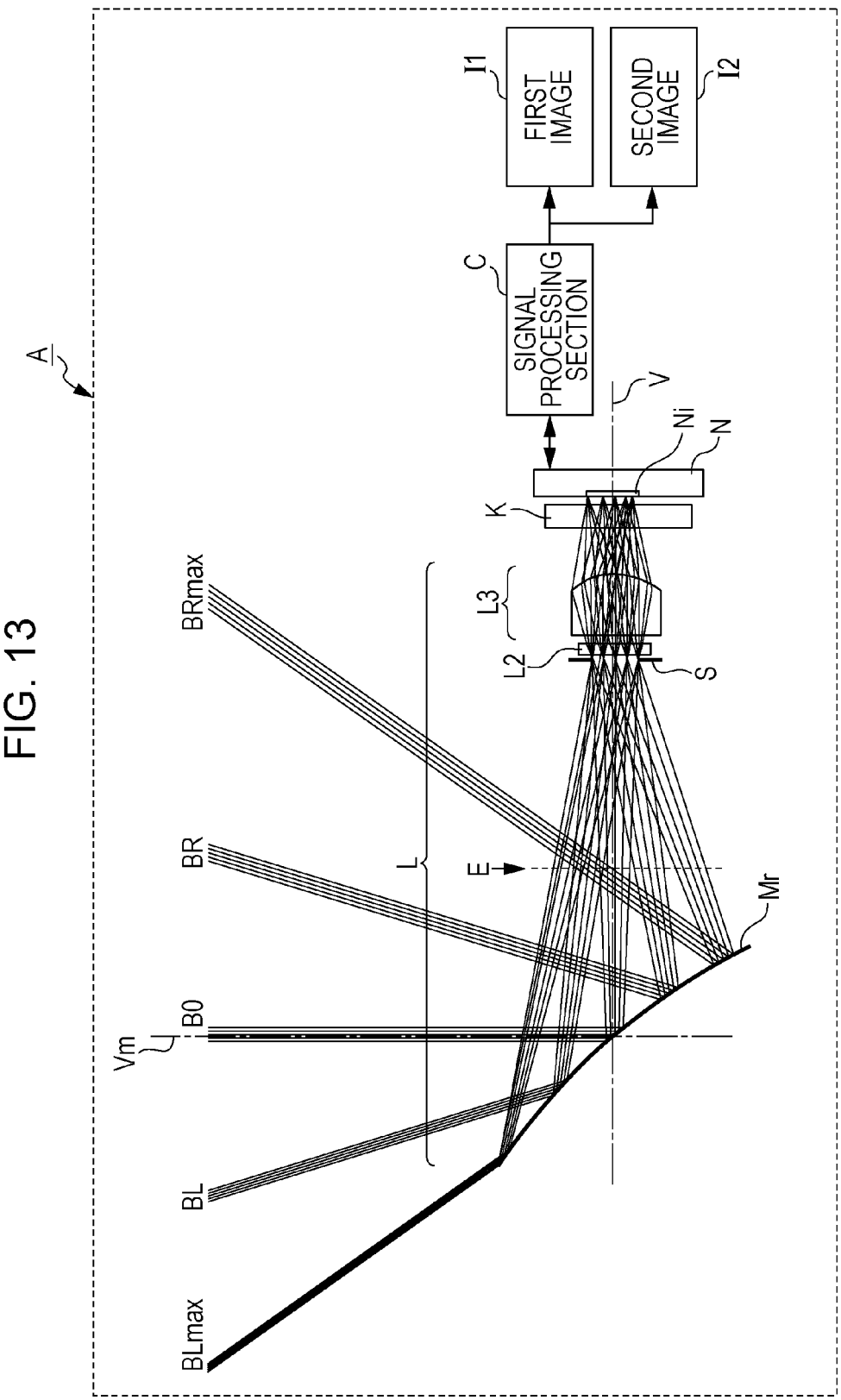
FIG. 13 is a schematic diagram depicting the configuration of an imaging device in Embodiment 4.

An imaging device of this embodiment differs from the imaging device of Embodiment 1 in that a mirror is provided in a lens optical system. Hereinafter, a component element which is different from the counterpart thereof in Embodiment 1 will be described. FIG. 13 is a schematic diagram depicting an imaging device A of Embodiment 4. The imaging device A of this embodiment includes a lens optical system L including a mirror Mr, an optical element array K positioned near the focus of the lens optical system L, an image sensor N, and a signal processing section C.

The lens optical system L is formed of the mirror Mr, a diaphragm S, an optical filter L2, and a second element optical system L3. The light beam direction of the light that has entered the imaging device A from an object (not depicted in the drawing) is bent by the mirror Mr, and an unnecessary light beam is removed by the diaphragm S. The optical filter L2 has regions D1 and D2 that allow respectively narrow wavelength bands having different wavelengths λ1 and λ2 as the peaks thereof to pass therethrough and is positioned near the diaphragm S.

Moreover, in FIG. 13, a pencil of rays B0 that forms an image on the center of the diagonal lines of the image sensor N travels from the object along the optical axis Vm, is reflected by the mirror Mr, and then travels along the optical axis V. The front face of the imaging device A is on an extension of the optical axis Vm. Each of pencils of rays BL and BR is an arbitrary pencil of rays that enters the imaging device A from an object located in an oblique direction (an angle which each of the pencils of rays BL and BR forms with the optical axis Vm is ωm), and each of pencils of rays BLmax and BRmax is a pencil of rays that enters the imaging device A from an object at the maximum angle of view (an angle which each of pencils of rays BLmax and BRma forms with the optical axis Vm is ωmmax) of the imaging device A. The pencil of rays B0 is reflected by the mirror Mr and reaches the diaphragm S and the optical filter L2. In FIG. 13, of the pencil of rays B0, a pencil of rays closer to the left side than the optical axis Vm passes through the region D1. Moreover, a pencil of rays closer to the right side than the optical axis Vm passes through the region D2. Then, the pencil of rays B0 passes through the second element optical system L3 and the optical element array K in this order and reaches an imaging surface Ni on the image sensor N. The same goes for the pencils of rays BL, BR, BLmax, and BRmax.

In the imaging device of this embodiment, as depicted in FIG. 13, since an entrance pupil E is located in a position closer to the object than the diaphragm S and the optical filter L2 near the diaphragm S, if the angles at which main light beams BLc and BRc of the pencils of rays BL and BR, the main light beams BLc and BRc passing through the center of the diaphragm, enter the optical filter L2 are assumed to be θLc and θRc, respectively, ωm>θLc and ωm>θRc hold. That is, a necessary and sufficient condition for ωm>θLc and ωm>θRc is that the entrance pupil E is located in a position closer to the object than the diaphragm S. This produces the effect of making the angle of a pencil of rays entering the optical filter L2 from the object closer to the optical axis V, that is, the normal of the optical filter L2. The angle θc becomes smaller as the entrance pupil E gets away from the diaphragm S and closer to the object and it is possible to make the angle ωmax which each of the pencils of rays BLmax and BRmax forms with the optical axis Vm greater, the pencils of rays BLmax and BRmax entering the imaging device at the greatest angle from the side where the object is located, which makes it possible to implement the imaging device as a wider-angle imaging device.

Incidentally, it is preferable that the mirror Mr is a convex mirror. This makes it easier to make the entrance pupil E get closer to the object than the diaphragm S. Moreover, a lens or another mirror may be provided between the mirror Mr and the optical filter L2, Furthermore, the imaging device may be configured such that no second element optical system L3 is provided and an image is taken by an element optical system and the diaphragm S, the element optical system including at least the mirror Mr.

Incidentally, since the mirror is used, this embodiment is an asymmetrical imaging optical system with respect to the optical axis V. When an axisymmetric optical system is used in the second element optical system, even the pencils of rays BL and BR that have entered the imaging device at the same angle of view have different image heights on the imaging surface Ni on the image sensor N. By performing asymmetrical correction on the distortion in the image by the signal processing section C, it is possible to obtain an image having left-right or top-bottom symmetry.

(Embodiment 5)

Figure 14:
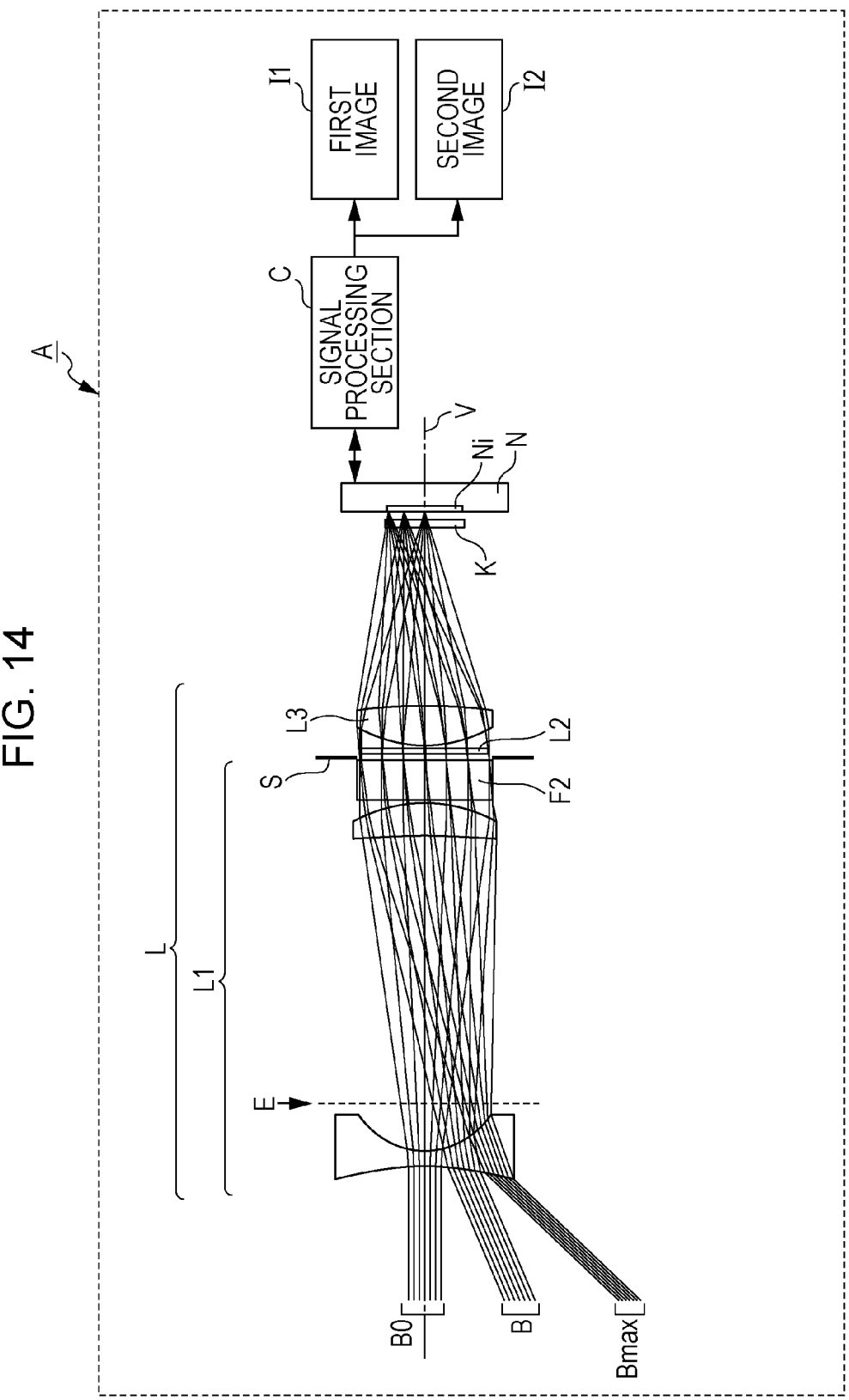
FIG. 14 is a schematic diagram depicting the configuration of an imaging device in Embodiment 5.

An imaging device of this embodiment differs from the imaging device of Embodiment 1 in that light beams from an object are converted into approximately-parallel lights by a first element optical system L1, that is, collimated thereby. Hereinafter, a component element which is different from the counterpart thereof in Embodiment 1 will be described. FIG. 14 is a schematic diagram depicting an imaging device A of Embodiment 5. The imaging device A of this embodiment includes a lens optical system L, an optical element array K positioned near the focus of the lens optical system L, an image sensor N, and a signal processing section C.

In this embodiment, the "approximately-parallel lights" refer to, for example, lights between which a difference in light beam direction is 5 degrees or less.

The lens optical system L is formed of a first element optical system L1 having at least one lens, a diaphragm S, an optical filter L2, and a second element optical system L3. The light beam direction of the light that has entered the lens optical system L from an object (not depicted in the drawing) is bent by the first element optical system L1, and an unnecessary light beam is removed by the diaphragm S.

Incidentally, in FIG. 14, an auxiliary filter F2 is provided on the side of the diaphragm S where the object is located. The auxiliary filter F2 has the function of preventing a light of a wavelength band that cannot be removed by the optical filter L2 from reaching the optical filter L2 by reflecting or absorbing such a light. The auxiliary filter F2 can be used also in other embodiments such as Embodiment 1.

Moreover, in FIG. 14, a pencil of rays B0 is a pencil of rays entering the imaging device A from an object located in front of the imaging device A, that is on an extension of an optical axis V, a pencil of rays B is an arbitrary pencil of rays entering the imaging device A from an object located in an oblique direction (an angle which the pencil of rays B forms with the optical axis V is ω), and a pencil of rays Bmax is a pencil of rays entering the imaging device A from an object at the maximum angle of view (an angle which the pencil of rays Bmax forms with the optical axis V is ωmax) of the imaging device A.

The pencil of rays B0 passes through the first element optical system L1 and reaches the diaphragm S and the optical filter L2 as an approximately-parallel light. In FIG. 14, a pencil of rays of the pencil of rays B0, the pencil of rays above the optical axis V, passes through the region D1. Moreover, a pencil of rays of the pencil of rays B0, the pencil of rays below the optical axis V, passes through the region D2. Then, the pencil of rays B0 passes through the second element optical system L3 and the optical element array K in this order and reaches an imaging surface Ni on the image sensor N. The same goes for the pencils of rays B and Bmax.

Figure 15:
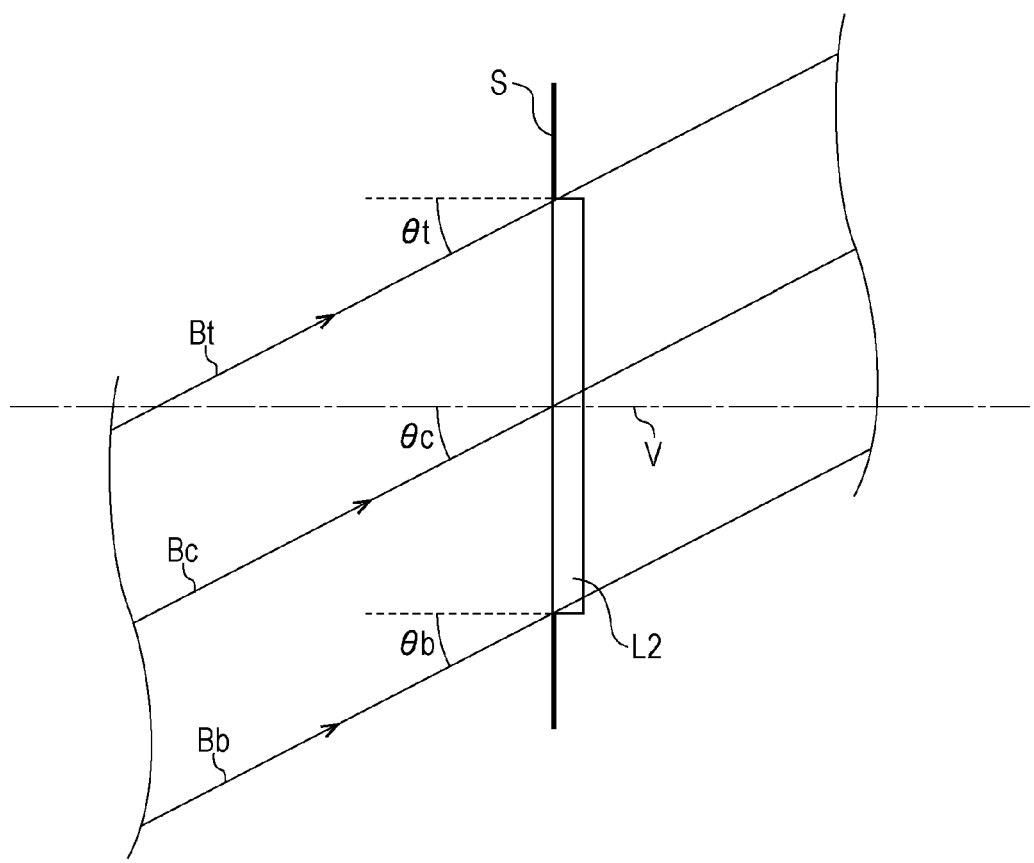
FIG. 15 is an enlarged view of a portion of Embodiment 5, the portion in which a pencil of rays entering the imaging device from an object enters an optical filter.

FIG. 15 is an enlarged view of a portion in which the pencil of rays B entering the imaging device from the object enters the optical filter L2. The angles θc, θt, and θb at which a main light beam Bc passing through the center of the diaphragm, a light beam Bt passing through the upper end of the diaphragm, and a light beam Bb passing through the lower end of the diaphragm respectively enter the optical filter L2 are almost the same angle. As a result, the light beams enter both the region D1 and the region D2 of the optical filter L2 at an angle of almost θc. Therefore, the wavelengths of the light beams passing through the regions D1 and D2 rarely shift depending on the position in the regions through which the light beams pass and are mixed as a result of being collected when they reach the pixels P1 and P2. Thus, this embodiment is suitable for obtaining a spectral image in a narrow wavelength band.

Moreover, as depicted in FIG. 14, an entrance pupil E is located in a position closer to the object than the diaphragm S and the optical filter L2 near the diaphragm S. At this time, ω>θc holds, That is, a necessary and sufficient condition for ω>θc is that the entrance pupil E is located in a position closer to the object than the diaphragm S. This produces the effect of making the angle of a pencil of rays entering the imaging device from the object closer to the optical axis V. The angle θc becomes smaller as the entrance pupil E gets away from the diaphragm S and closer to the object and it is possible to make the angle ωmax which the pencil of rays Bmax forms with the optical axis V greater, the pencil of rays Bmax entering the imaging device at the greatest angle from the side where the object is located, which makes it possible to implement the imaging device as a wider-angle imaging device.

The greater the angle which a pencil of rays from the object forms with the optical axis V, the greater the angle θc. That is, the angle θc becomes the greatest in the pencil of rays Bmax, and, in the pencil of rays B0, the angle θc comes closer to a state in which it is parallel to the optical axis V. As is clear from Expression (1), the greater the angle of incidence to a filter, the wavelength λ passing through the filter shifts to the short wavelength side. In consideration of this, it is preferable to select a wavelength between a transmission wavelength of a pencil of rays entering the imaging device from the object along the optical axis V, that is, the normal of the filter and a transmission wavelength of a pencil of rays entering the imaging device at the maximum angle of view ωmax as transmission wavelength bands of the regions D1 and D2 because this makes it possible to acquire an image of a wavelength in an extremely narrow band, The imaging device of this embodiment has an advantage that the size of the imaging device in an optical axis direction, in particular, can be reduced when, in particular, image acquisition requiring a high degree of wavelength precision is performed. For example, if the angles θc, θt, and θb of incidence to the optical filter L2 are different from one another as in FIG. 7, it is necessary to make θc, θt, and θb smaller, and therefore the imaging device inevitably gets longer in the optical axis. In the imaging device of this embodiment, since the angles of incidence θc, θt, and θb are almost the same, such restrictions can be alleviated and the imaging device can be made smaller.

Incidentally, in the first element optical system L1, it is preferable that at least one lens has negative light-collecting power. This makes it easier to make the entrance pupil E get closer to the object than the diaphragm S.

In this embodiment, the second element optical system L3 is formed of one lens, but the second element optical system L3 may be formed of optical parts such as a plurality of lenses.

Moreover, in this embodiment, for example, an example in which conversion is performed to obtain approximately-parallel lights between which a difference in light beam direction is 5 degrees or less has been described, but the example is not limited thereto. When a pencil of rays entering the imaging device at the maximum angle of view enters the first region of the optical filter L2, the maximum value (for example, a difference between θt and θc in FIG. 15) of differences between the angles of incidence of the light beams included in the pencil of rays simply has to be smaller than the maximum value (for example, θt or θc, whichever is greater, in FIG. 15) of the angles of incidence of the light beams included in the pencil of rays. Likewise, when a pencil of rays entering the imaging device at the maximum angle of view enters the second region of the optical filter L2, the maximum value (for example, a difference between θc and θb in FIG. 15) of differences between the angles of incidence of the light beams included in the pencil of rays simply has to be smaller than the maximum value (for example, θc or θb, whichever is greater, in FIG. 15) of the angles of incidence of the light beams included in the pencil of rays. As described above, if variations in the angles of incidence of the light beams entering the optical filter are smaller than the maximum value of the angles of incidence, it is necessary simply to make the maximum angle of incidence smaller, which makes it possible to alleviate restrictions at the time of design and achieve reduction in size.

(Embodiment 6)

An imaging device of this embodiment differs from the imaging device of Embodiment 5 in that no optical element array is provided, the focus of a lens optical system L is located on an imaging surface Ni of an image sensor N, an optical element is formed of two optical filters: an optical filter L2a and an optical filter L2b, and the optical filters L2a and L2b are fixed to a movable holder H.

Figure 16:
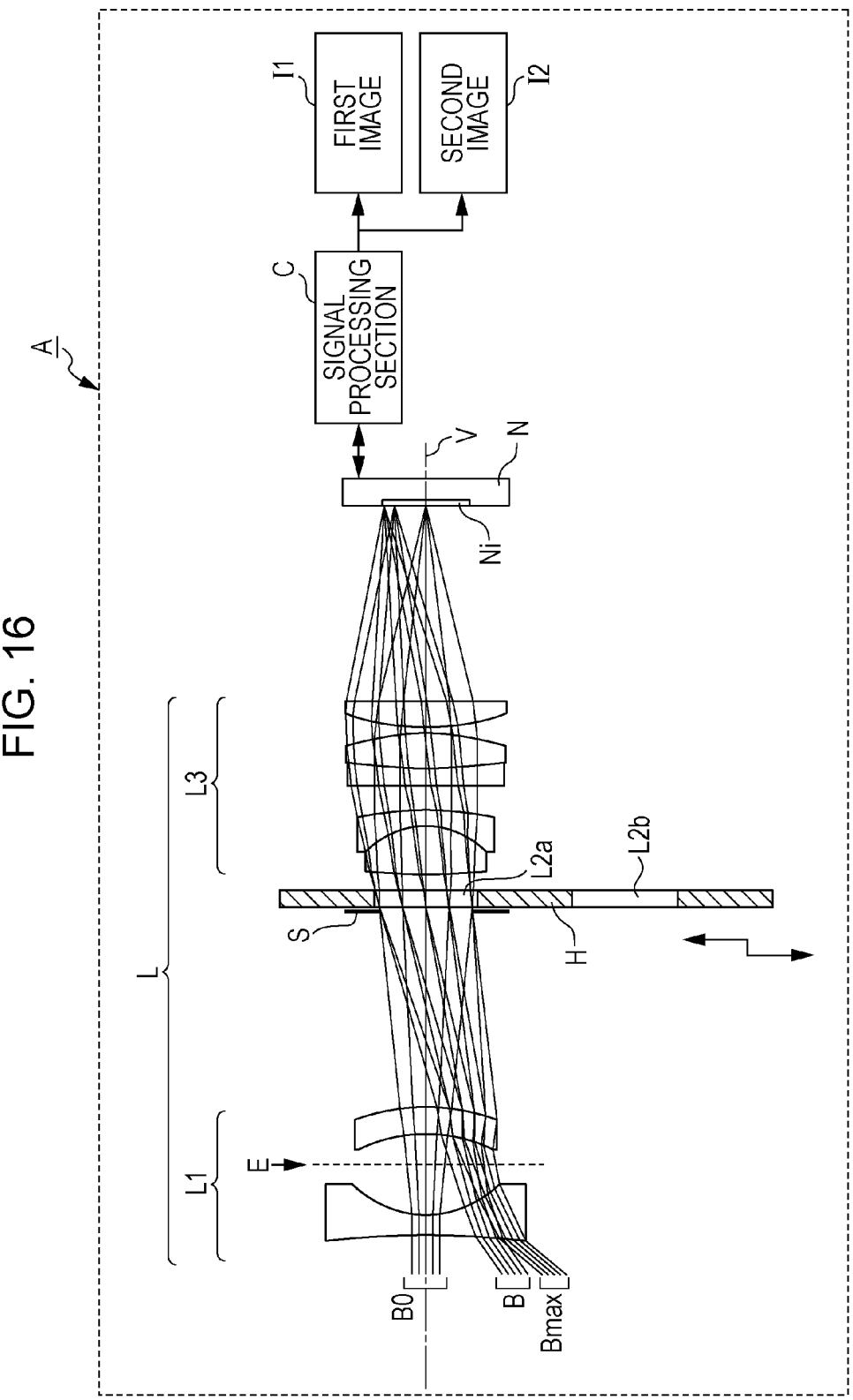
FIG. 16 is a schematic diagram depicting the configuration of an imaging device in Embodiment 6.

FIG. 16 depicts a state in which an optical axis V passes through the optical filter L2a, the state in which the light beam direction of the light entering the imaging device from an object is bent by a first element optical system L1, an unnecessary light beam is removed by a diaphragm S, and the light enters the optical filter L2a. The optical filter L2a allows a narrow wavelength band with a wavelength λa as the peak thereof to pass therethrough. An arbitrary pencil of rays B entering an imaging device A from an object located in an oblique direction (an angle which the pencil of rays B forms with the optical axis V is ω) enters the optical filter L2a in a layout similar to that of FIG. 7 of Embodiment 1. The angles of light beams entering the optical filter L2a are expressed as θc, θt, and θb for a main light beam Bc passing through the center of the diaphragm, a light beam Bt passing through the upper end of the diaphragm, and a light beam Bb passing through the lower end of the diaphragm, respectively. The angles θc, θt, and θb are different angles and have the relationship θt>θc>θb. As a result, light beams enter the optical filter L2a at an angle between θb and θt and become light beams having different wavelengths after passing through the optical filter L2a due to different angles of incidence, but these light beams are mixed as a result of being collected when they reach pixels P1 and P2. As the aperture shape of the diaphragm S, a circular shape, a rectangular shape, or the like is used; in either case, the proportion of the main light beam passing through the center of the diaphragm is high and the heaviest weight is assigned thereto when the light beam reaches the pixel. It is for this reason that actually no problem arises even when the pencil of rays B is considered to enter the optical filter L2a apparently at an angle corresponding to the angle θc of the main light beam.

In the imaging device of this embodiment, as depicted in FIG. 16, an entrance pupil E is located in a position closer to the object than the diaphragm S and the optical filter L2a near the diaphragm S. At this time, ω>θc holds. That is, a necessary and sufficient condition for ω>θc is that the entrance pupil E is located in a position closer to the object than the diaphragm S. This produces the effect of making the angle of a pencil of rays entering the imaging device from the object closer to the optical axis V, that is, the normal of the optical filter L2a. The angle θc becomes smaller as the entrance pupil E gets away from the diaphragm S and closer to the object and it is possible to make the angle ωmax which the pencil of rays Bmax forms with the optical axis V greater, the pencil of rays Bmax entering the imaging device at the greatest angle from the side where the object is located, which makes it possible to implement the imaging device as a wider-angle imaging device.

Next, by operating the holder H, the state is changed to a state in which the optical axis V passes through the optical filter L2b. The optical filter L2b allows a narrow wavelength band with a wavelength λb as the peak thereof to pass therethrough. The angle at which an arbitrary pencil of rays B entering the imaging device A from an object located in an oblique direction (an angle which the pencil of rays B forms with the optical axis V is ω) enters the optical filter L2b is the same as the angle at which the pencil of rays B enters the optical filter L2a, and the same effect is produced except for a different wavelength of an image to be obtained. A signal processing section C obtains two types of images in cooperation with the operation of the holder H and outputs these images as a first image I1 and a second image I2.

Incidentally, in this embodiment, the lens optical system L of the imaging device of Embodiment 1 is used; however, this embodiment is also effective for other lens optical systems including Embodiment 2 and the embodiments that follow. The number of types of optical elements is not limited to two. Moreover, the holder H is not limited to a sliding holder, and a rotary wheel-type holder may be adopted.

In particular, the lens optical system L of Embodiment 5 has the advantage that, since the use thereof makes the angles θc, θt, and θb at which light beams enter the optical filter L2 become almost the same angle, the size of the imaging device in an optical axis direction can be reduced when image acquisition requiring a high degree of wavelength precision is performed.

(Embodiment 7)

Figure 17:
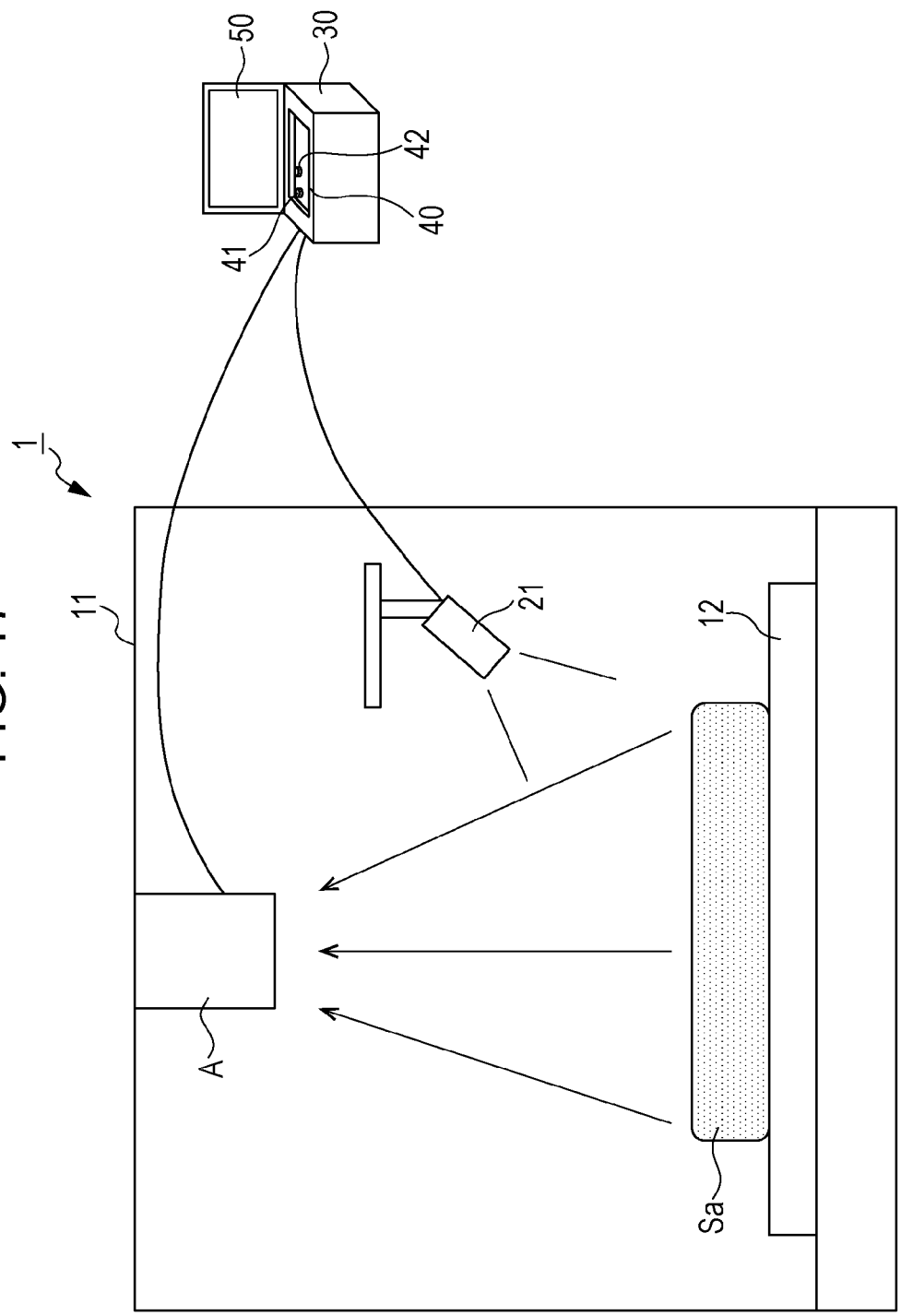
FIG. 17 is a schematic diagram of the overall structure of a food analyzing apparatus of Embodiment 7.

An analyzing apparatus using the imaging devices described in Embodiments 1 to 6 will be hereinafter described. FIG. 17 is a schematic diagram of the overall structure of a food analyzing apparatus of this embodiment.

A food analyzing apparatus 1 has a housing 11, a table 12, an imaging device A, a processor 30, an operating section 40, and a display section 50.

The table 12 and the imaging device A are positioned in the housing 11. On the table 12, an object to be measured Sc is positioned. Incidentally, the food analyzing apparatus 1 can analyze one or a plurality of foods as the object to be measured Sa. Moreover, the food analyzing apparatus 1 can also analyze a food in a container or the like as the object to be measured Sa.

The imaging device A has a light source 21 that irradiates the object to be measured Sa positioned on the table 12 with a light. The imaging device A has the function of receiving the light reflected from the object to be measured Sa and performing imaging.

The light source 21 is placed in a position in which the light source 21 can irradiate the whole of the object to be measured Sa with a light. The light emitted from the light source 21 includes some of wavelengths of at least 700 to 2500 nm. As the light source 21, for example, a halogen lamp, an LED, a laser, or the like is used.

The imaging device A acquires an image with a first specific wavelength, an image with a second specific wavelength, and an image with a third specific wavelength.

The first to third specific wavelengths are determined by an experiment or the like based on the spectral information of a plurality of foods whose ingredients are known. Specifically, based on the relationship between the ratio of a specific ingredient in a plurality of foods and the absorbance, a wavelength well reflecting the ratio of the specific ingredient in foods is determined as a specific wavelength.

As the first specific wavelength, a wavelength having a strong correlation with protein as an ingredient is adopted. For example, as the first specific wavelength, 910 nm and a wavelength near this wavelength can be adopted.

As the second specific wavelength, a wavelength having a strong correlation with lipid as an ingredient is adopted. For example, as the second specific wavelength, 930 nm and a wavelength near this wavelength can be adopted.

As the third specific wavelength, a wavelength having a strong correlation with carbohydrate as an ingredient is adopted. For example, as the third specific wavelength, 980 nm and a wavelength near this wavelength can be adopted.

As an image sensor of the imaging device A, for example, an element using silicon having sensitivity over a wide range in a near-infrared region and indium/gallium/arsenic, the element that can convert the amount of light into an electrical signal, can be used.

With reference to FIG. 17, the electrical configuration of the food analyzing apparatus 1 will be described.

The operating section 40 has a measurement button 41 and a switching button 42. When the measurement button 41 is pressed, the operating section 40 outputs, to the processor 30, a signal indicating that the measurement button 41 has been pressed. When the switching button 42 is pressed, the operating section 40 outputs, to the processor 30, a signal indicating that the switching button 42 has been pressed.

When receiving the signal indicating that the measurement button 41 has been pressed, the processor 30 controls the imaging device A and starts the analysis of the object to be measured Sa. When receiving the signal indicating that the switching button 42 has been pressed, the processor 30 changes the contents which the display section 50 is made to display.

The processor 30 makes the light source 21 momentarily irradiate the object to be measured Sa with a light including a near-infrared light. The light scattered or reflected from the object to be measured Sa enters the imaging device A.

The imaging device A acquires an image with the first specific wavelength, an image with the second specific wavelength, and an image with the third specific wavelength without displacement. Thus, the outputs of the pixels forming the image with the first specific wavelength, the image with the second specific wavelength, and the image with the third specific wavelength reflect part of protein, lipid, and carbohydrate in the object to be measured. That is, the imaging device A outputs, to the processor 30 (see FIG. 17), a signal reflecting part (hereinafter a "measurement site") of protein, lipid, and carbohydrate in the object to be measured Sa which is the starting point of the light beam which the imaging device A receives.

The processor 30 performs computations to obtain the ratio and amount of protein based on the output of the image with the first specific wavelength and a previously stored relational expression.

The processor 30 performs computations to obtain the ratio and amount of lipid based on the output of the image with the second specific wavelength and a previously stored relational expression.

The processor 30 performs computations to obtain the ratio and amount of carbohydrate based on the output of the image with the third specific wavelength and a previously stored relational expression.

Incidentally, each relational expression can be determined in advance by, for example, using PLS based on the relationship between the absorbance (the amount of light) at each wavelength of a plurality of foods containing the above ingredients and the ratio of each ingredient.

The calorie of a food is obtained by multiplying each of the amount of protein, the amount of lipid, and the amount of carbohydrate by a calorie coefficient and summing the results. It is for this reason that the processor 30 performs computations to obtain the calorie of each measurement site based on the amount of protein, the amount of lipid, and the amount of carbohydrate in each measurement site. Incidentally, the ratio of protein, the amount of protein, the ratio of lipid, the amount of lipid, the ratio of carbohydrate, the amount of carbohydrate, and the calorie in each measurement site correspond to "partial nutrition information".

The processor 30 creates, as distribution image information, distribution image information indicating the calorie and distribution image information indicating the ingredient. The processor 30 outputs the distribution image information to the display section 50 and makes the display section 50 display a distribution image P. Moreover, based on the output of the operating section 40, the processor 30 performs switching between the distribution image information indicating the calorie and the distribution image information indicating the ingredient, the distribution image information to be output to the display section 50.

Figure 18:
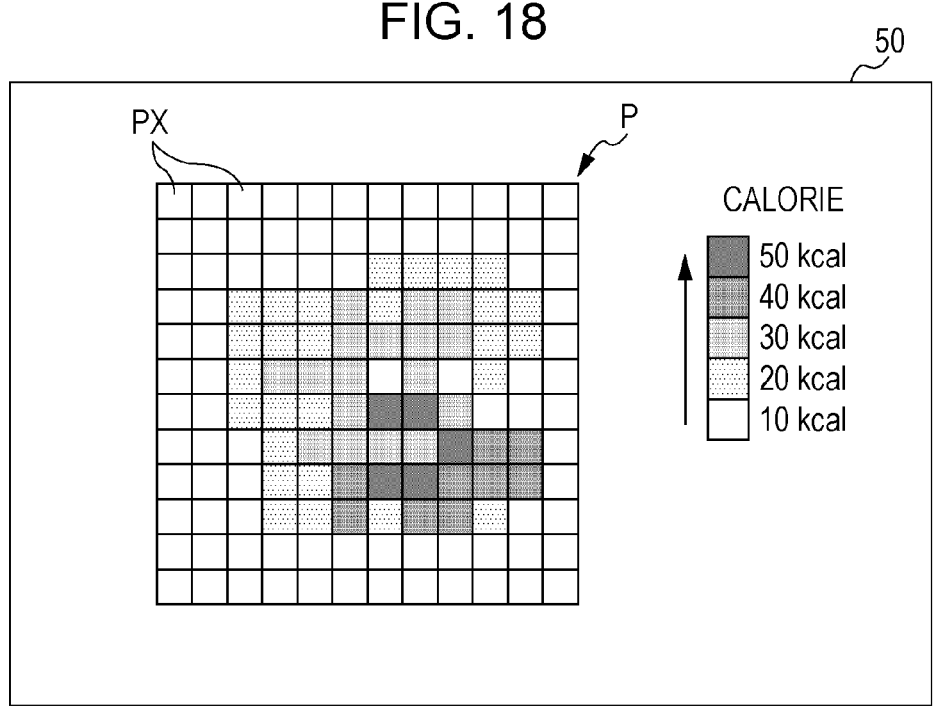
FIG. 18 is a front view depicting a display example of a calorie distribution image displayed in a display section of Embodiment 7.
Figure 19:
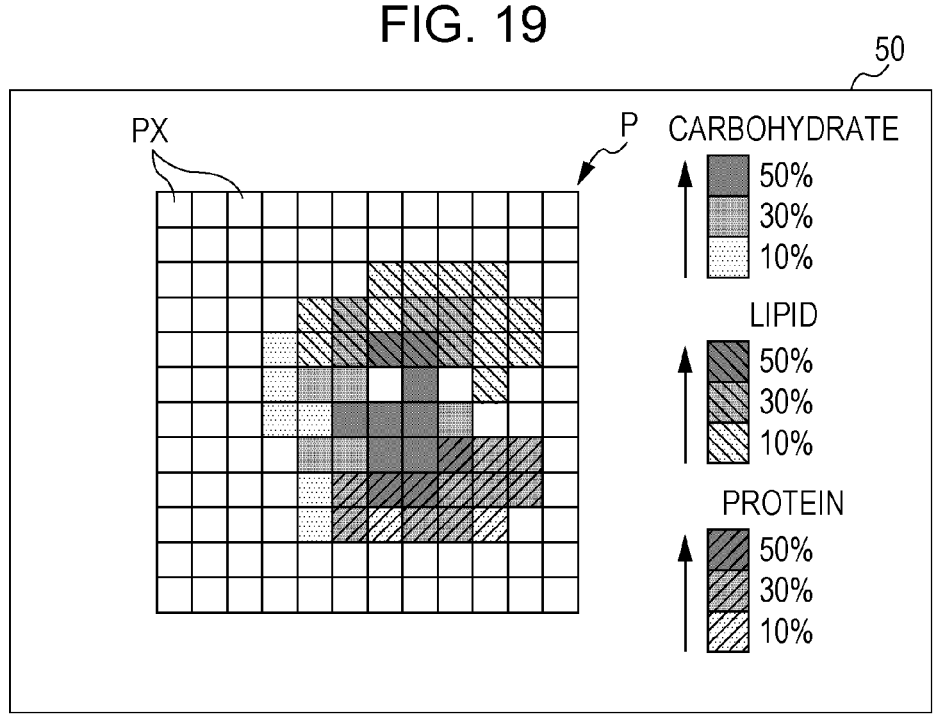
FIG. 19 is a front view of a display example of an ingredient distribution image displayed in the display section of Embodiment 7.

With reference to FIGS. 18 and 19, the distribution image P will be described. Incidentally, in FIGS. 18 and 19, the density of dots of dot hatching indicates the density of a display color. Moreover, in FIG. 19, the presence or absence and the direction of lines of line hatching indicate the difference in display color.

As depicted in FIG. 18, the calorie distribution image P is divided into a plurality of partial regions PX. One partial region PX indicates one piece of partial nutrition information. The relative position of each partial region PX in the distribution image P corresponds to the relative position of a measurement site in the object to be measured Sa, the measurement site related to the partial nutrition information displayed in each partial region PX.

The calorie distribution image P visually expresses the magnitude of the calorie of each partial region PX by relating the density of a display color of each partial region PX to the magnitude of the calorie.

As depicted in FIG. 19, the ingredient distribution image P visually expresses an ingredient of carbohydrate, lipid, and protein, the ingredient with the largest ratio, in each partial region PX by using display colors that differ from one ingredient to another. Moreover, by relating the density of a display color of each partial region PX to the ratio of the ingredient, the ratio of the ingredient in each partial region PX is visually expressed.

The operation of the food analyzing apparatus 1 will be described.

In a virtual food analyzing apparatus that numerically displays the calorie and the ingredients of the whole of an object to be measured Sa, for example, if the calorie or the ratio of an ingredient of the object to be measured Sa is higher than the user's target calorie or ratio of the ingredient, the user removes part of the object to be measured Sa and repeats the operation of performing the analysis by the food analyzing apparatus again. This requires a good deal of user's efforts.

Since the food analyzing apparatus 1 displays the distribution image P in the display section 50, the user can easily figure out the distribution of the calorie and ingredients of the object to be measured Sa. As a result, if the calorie or the ratio of an ingredient of the object to be measured Sa is higher than the user's target calorie or ratio of the ingredient, the user can easily figure out which part and how much part of the object to be measured Sa the user should remove to attain the target calorie or ratio of the ingredient. This improves the convenience of the user. Moreover, it is possible to attain the target calorie or ratio of the ingredient in a short time. This makes it possible to prevent the taste, shape, and so forth of the food from changing as a result of the food being altered by temperature, for example, due to a time-consuming adjustment.

In the virtual food analyzing apparatus that numerically displays the calorie and the ingredients of the whole of an object to be measured Sa, when the user performs analysis of a plurality of foods, for example, the user repeats the operation of performing the analysis for each food. This requires a good deal of user's efforts.

Since the food analyzing apparatus 1 displays the distribution image P in the display section 50, it is possible to figure out the calorie and ingredients of each of a plurality of foods by one measurement. This improves the convenience of the user.

The food analyzing apparatus 1 of this embodiment has the following advantages.

(1) The food analyzing apparatus 1 displays the distribution image P in the display section 50. This makes it easier for the user to figure out the distribution of partial nutrition information including the calorie and ingredients of an object to be measured Sa.

(2) The food analyzing apparatus 1 can obtain the partial nutrition information of the whole of the object to be measured Sa by computation by the imaging device A in a short time. As described in Embodiments 1 to 6, the imaging device A makes it possible to maintain a near-infrared spectral wavelength at a high degree of accuracy even at the time of acquisition of a wide-angle image and thereby perform a high-accuracy calorie analysis. The wide angle makes it possible to take an image of the object to be measured Sa at close range, making it possible to reduce the size of the food analyzing apparatus 1.

(3) The food analyzing apparatus 1 makes the light source 21 emit a light momentarily. This makes the object to be measured Sa less likely to be warmed by the light or changed such as undergoing degeneration.

(4) The food analyzing apparatus 1 analyzes the object to be measured Sa nondestructively. This makes it possible to use the object to be measured Sa after measurement for food as it is.

(5) The food analyzing apparatus 1 analyzes the object to be measured Sa by using a near-infrared light. This makes it possible to perform an analysis without equipment such as a centrifugal machine which is used when a chemical analysis of the object to be measured Sa is performed by crushing the object to be measured Sa, a reagent, and so forth.

In this embodiment, the food analyzing apparatus equipped with any one of the imaging devices described in Embodiments 1 to 6 has been described, but an apparatus equipped with the imaging device is not limited thereto. All the apparatuses and systems that acquire an image having a plurality of optical information for an optical element having an incident angle dependence and use the image can acquire subject information at a high degree of accuracy as small apparatuses and systems.

Moreover, if necessary, a plurality of imaging devices described in Embodiments 1 to 6 may be installed or another camera having the function of, for example, acquiring a color image may be additionally used. Alternatively, the imaging device A may be provided with the function of acquiring color spectral information such as R, G, and B.

As described above, the imaging device according to the present disclosure includes an optical system (a lens optical system L) having lenses L1 and L3 and a diaphragm S, an image sensor N having first to nth pixels which the light that has passed through the optical system L enters, and an optical element array K positioned between the optical system and the image sensor N. The optical system L has an optical filter L2 having a first region and a second region having different optical characteristics. The optical element array K makes the light that has passed through the first region enter the first pixel and makes the light that has passed through the second region enter the second pixel. An entrance pupa E of the optical system L is located between the diaphragm S and an object.

This makes it possible to perform spectroscopic imaging in a narrow wavelength band at a wide angle of view. More specifically, it is possible to implement an imaging device that maintains a spectral wavelength at a high degree of accuracy even at the time of acquisition of a wide-angle image. The wide angle makes it possible to increase an object target area and reduce the number of imaging devices. Moreover, since it is possible to take an image of a target subject at dose range, it is possible to reduce the sizes of a system and an analyzing apparatus which are equipped with the imaging device.

Here, the optical system L may have a first element optical system L1 having negative light-collecting power, the first element optical system L1 guiding the incident light to the diaphragm S and the optical filter L2.

Here, the first element optical system L1 may have a concave lens.

Here, the first element optical system L1 may have a mirror Mr with a convex surface, the mirror Mr reflecting the incident light toward the diaphragm S and the optical filter L2.

Here, when a pencil of rays entering the imaging device at the maximum angle of view enters the first region of the optical filter L2, the maximum value of differences between the angles of incidence of the light beams included in the pencil of rays may be smaller than the maximum value of the angles of incidence of the light beams included in the pencil of rays, and, when the pencil of rays entering the imaging device at the maximum angle of view enters the second region of the optical filter L2, the maximum value of differences between the angles of incidence of the light beams included in the pencil of rays may be smaller than the maximum value of the angles of incidence of the light beams included in the pencil of rays.

Here, a holder H that interchangeably holds at least one of the first region and the second region in the optical filter L2 above an optical axis of the optical system may be further provided.

Here, the optical filter L2 may be a spectral filter or a polarizing filter.

Here, a lenticular lens may be positioned in a plane of the optical element array K, the plane facing the image sensor N.

Here, a microlens array may be positioned in a plane of the optical element array K, the plane facing the image sensor N.

Here, the optical element array Ni may be positioned on the image sensor N.

Here, microlenses provided between the optical element array and the image sensor may be further provided, and the optical element array may be positioned on the image sensor with the microlenses positioned between the optical element array and the image sensor.

Moreover, an analyzing apparatus according to the present disclosure includes a light source that irradiates an object to be analyzed with a light, the above-described imaging device that receives at least one of a group of a light reflected from the object to be analyzed, a light scattered from the object to be analyzed, and a light that has passed through the object to be analyzed, and a processor that performs computation on the light received by the imaging device.

Moreover, another analyzing apparatus according to the present disclosure includes a light source that irradiates an object to be analyzed with a light including at least part of near-infrared wavelengths of 700 nm or more, the above-described imaging device that receives at least one of a light reflected from the object to be analyzed and a light that has passed through the object to be analyzed, a processor that obtains the amount of absorbed light of the light received by the imaging device by computation, and an analyzer that performs at least one of calculating the calorie of the object to be analyzed based on the correlation between the amount of absorbed light and the calorie and the amount of absorbed light obtained by the processor by computation and calculating the ingredient amount of the object to be analyzed based on the correlation between the amount of absorbed light and the ingredient amount of a food and the amount of absorbed light obtained by the processor by computation.

While the imaging device and the analyzing apparatus according to one aspect of the present disclosure has been described based on the embodiments, the present disclosure is not limited to these embodiments. What is obtained by applying various modifications conceived of by a person skilled in the art to the embodiments or any configuration obtained by combining the component elements in different embodiments is also included in the scope of one or a plurality of aspects of the present disclosure within the scope of the present disclosure.

The imaging device according to the present disclosure is especially useful for the purpose of acquiring a spectral image or a polarization image and performing sensing. The range of application of the imaging device includes a food analyzing apparatus, various product inspection lines, medical uses, and so forth, and the imaging device can sense useful information in a wide range of application area and reduce the sizes of equipment and systems. Moreover, the imaging device according to the present disclosure can also be applied to the uses such as a car-mounted camera, a security camera, biometric authentication, a microscope, and an astronomical telescope.

What is claimed is:

1. An imaging device used to take an image of an object, the imaging device comprising:
   an optical system including an optical filter, a first element optical system, a lens and a diaphragm;
   an image sensor having a first pixel and a second pixel which a light that has passed through the optical system enters; and
   an optical element array positioned between the optical system and the image sensor, wherein
   the optical filter includes a first region and a second region having different optical characteristics,
   the optical element array makes a light that has passed through the first region enter the first pixel and makes a light that has passed through the second region enter the second pixel,
   an entrance pupil of the optical system is located between the diaphragm and the object,
   the first element optical system includes a mirror with a convex surface, has negative light-collecting power and guides an incident light to the diaphragm and the optical filter, and
   the minor reflects the incident light toward the diaphragm and the optical filter.

2. The imaging device according to claim 1, wherein the optical filter is a spectral filter or a polarizing filter.

3. The imaging device according to claim 1, wherein a lenticular lens is positioned in a plane of the optical element array, the plane facing the image sensor.

4. The imaging device according to claim 1, wherein a microlens array is positioned in a plane of the optical element array, the plane facing the image sensor.

5. The imaging device according to claim 1, wherein the optical element array is positioned on the image sensor.

6. The imaging device according to claim 5, further comprising:
microlenses positioned between the optical element array and the image sensor, wherein
the optical element array is positioned on the image sensor with the microlenses positioned between the optical element array and the image sensor.

7. An analyzing apparatus comprising:
a light source that irradiates an object to be analyzed with a light;
the imaging device according to claim 1, the imaging device receiving at least one selected from the group consisting of a light reflected from the object to be analyzed, a light scattered from the object to be analyzed, and a light that has passed through the object to be analyzed; and
a processor that performs computation on the light received by the imaging device.

8. An analyzing apparatus comprising:
a light source that irradiates an object to be analyzed with a light including at least part of near-infrared wavelengths of 700 nm or more;
the imaging device according to claim 1, the imaging device receiving at least one selected from the group consisting of a light reflected from the object to be analyzed and a light that has passed through the object to be analyzed;
a processor that calculates an amount of absorbed light of the light received by the imaging device; and
an analyzer that performs at least one selected from the group consisting of calculating a calorie of the object to be analyzed based on a correlation between an amount of absorbed light and a calorie and based on the amount of absorbed light calculated by the processor and calculating an ingredient amount of the object to be analyzed based on a correlation between the amount of absorbed light and an ingredient amount of a food and based on the amount of absorbed light calculated by the processor.

9. An imaging device used to take an image of an object, the imaging device comprising:
an optical system including an optical filter, a lens and a diaphragm;
an image sensor having a first pixel and a second pixel which a light that has passed through the optical system enters; and
an optical element array positioned between the optical system and the image sensor, wherein
the optical filter includes a first region and a second region having different optical characteristics,
the optical element array makes a light that has passed through the first region enter the first pixel and makes a light that has passed through the second region enter the second pixel,
an entrance pupil of the optical system is located between the diaphragm and the object,
when a pencil of rays entering the imaging device at a maximum angle of view enters the first region of the optical filter, a maximum value of differences between angles of incidence of light beams included in the pencil of rays is smaller than a maximum value of the angles of incidence of the light beams included in the pencil of rays, and
when a pencil of rays entering the imaging device at a maximum angle of view enters the second region of the optical filter, a maximum value of differences between angles of incidence of light beams included in the pencil of rays is smaller than a maximum value of the angles of incidence of the light beams included in the pencil of rays.

10. The imaging device according to claim 9, wherein:
the optical system further includes a first element optical system, and
the first element optical system includes a concave lens, has negative light-collecting power and guides an incident light to the diaphragm and the optical filter.

11. The imaging device according to claim 9, wherein the optical filter is a spectral filter or a polarizing filter.

12. The imaging device according to claim 9, wherein a lenticular lens is positioned in a plane of the optical element array, the plane facing the image sensor.

13. The imaging device according to claim 9, wherein a microlens array is positioned in a plane of the optical element array, the plane facing the image sensor.

14. The imaging device according to claim 9, wherein the optical element array is positioned on the image sensor.

15. The imaging device according to claim 14, further comprising:
microlenses positioned between the optical element array and the image sensor, wherein
the optical element array is positioned on the image sensor with the microlenses positioned between the optical element array and the image sensor.

16. An imaging device used to take an image of an object, the imaging device comprising:
an optical system including a lens, a diaphragm and an optical filter that includes a first region and a second region, the first and second regions having different optical characteristics;
a holder that interchangeably holds at least one selected from the group consisting of the first region and the second region in the optical filter on an optical axis of the optical system;
an image sensor having a first pixel and a second pixel which a light that has passed through the optical system enters; and
an optical element array positioned between the optical system and the image sensor, wherein
the optical element array makes a light that has passed through the first region enter the first pixel and makes a light that has passed through the second region enter the second pixel, and
an entrance pupil of the optical system is located between the diaphragm and the object.

17. The imaging device according to claim 16, wherein:
the optical system further includes a first element optical system, and
the first element optical system includes a concave lens, has negative light-collecting power and guides an incident light to the diaphragm and the optical filter.

18. The imaging device according to claim 16, wherein the optical filter is a spectral filter or a polarizing filter.

19. The imaging device according to claim 16, wherein a lenticular lens is positioned in a plane of the optical element array, the plane facing the image sensor.

20. The imaging device according to claim 16, wherein a microlens array is positioned in a plane of the optical element array, the plane facing the image sensor.

21. The imaging device according to claim 16, wherein the optical element array is positioned on the image sensor.

22. The imaging device according to claim 16, further comprising:
    microlenses positioned between the optical element array and the image sensor, wherein
    the optical element array is positioned on the image sensor with the microlenses positioned between the optical element array and the image sensor.

* * * * *